(12) United States Patent
Mansky

(10) Patent No.: US 6,951,144 B2
(45) Date of Patent: Oct. 4, 2005

(54) HIGH THROUGHPUT MECHANICAL RAPID SERIAL PROPERTY TESTING OF MATERIALS LIBRARIES

(75) Inventor: Paul Mansky, San Francisco, CA (US)

(73) Assignee: Symyx Technologies, Inc., Santa Clara, CA (US)

(*) Notice: Subject to any disclaimer, the term of this patent is extended or adjusted under 35 U.S.C. 154(b) by 53 days.

(21) Appl. No.: 10/811,619

(22) Filed: Mar. 29, 2004

(65) Prior Publication Data

US 2004/0177707 A1 Sep. 16, 2004

Related U.S. Application Data

(62) Division of application No. 09/939,252, filed on Aug. 24, 2001, now abandoned.

(51) Int. Cl.[7] ................................................. G01L 3/00
(52) U.S. Cl. ................................................. 73/862.046
(58) Field of Search .......................... 73/760, 781, 788, 73/790, 794–798, 818, 863, 863.01, 863.11, 150 R, 150 A

(56) References Cited

U.S. PATENT DOCUMENTS

| | | | |
|---|---|---|---|
| 1,870,412 A | 8/1932 | Kennedy | |
| 3,071,961 A | 1/1963 | Heigl et al. | |
| 3,675,475 A | 7/1972 | Weinstein | |
| 3,713,328 A | 1/1973 | Aritomi | |
| 3,798,960 A | 3/1974 | Glass | |
| 3,805,598 A | 4/1974 | Corcoran | |
| 3,818,751 A | 6/1974 | Karper et al. | |
| 3,849,874 A | 11/1974 | Jeffers | |
| 3,895,513 A | 7/1975 | Richardson | |
| 3,908,441 A | 9/1975 | Virloget | |
| 3,933,032 A | 1/1976 | Tschoegl | |
| 4,229,979 A | 10/1980 | Greenwood | |
| 4,447,125 A | 5/1984 | Lazay et al. | |
| 4,517,830 A | 5/1985 | Gunn et al. | |
| 4,567,774 A | 2/1986 | Manahan et al. | |
| 4,570,478 A | 2/1986 | Soong | |
| 4,599,219 A | 7/1986 | Cooper et al. | |
| 4,602,501 A | 7/1986 | Hirata | |
| 4,605,589 A | 8/1986 | Orphanides | |
| 4,680,958 A | 7/1987 | Ruelle et al. | |
| 4,685,328 A | 8/1987 | Huebner et al. | |
| 4,699,000 A | 10/1987 | Lashmore et al. | |
| 4,715,007 A | 12/1987 | Fujita et al. | |
| 4,740,078 A | 4/1988 | Daendliker et al. | |
| 4,749,854 A | 6/1988 | Martens | |

(Continued)

OTHER PUBLICATIONS

U.S. Appl. No. 09/420,334 entitled "Graphic Design of Combinatorial Material Libraries" (Lacy, et al.) filed on Oct. 18, 1999.

U.S. Appl. No. 09/550,549 entitled "Automated Process Control And Data Management System And Methods" (Crevier, et al.) filed on Apr. 14, 2000.

U.S. Appl. No. 09/755,623 entitled "Laboratory Database System and Methods For Combinatorial Materials Research" (Dorsett, Jr. et al.) filed on Jan. 5, 2001.

(Continued)

Primary Examiner—Edward Lefkowitz
Assistant Examiner—Corey D. Mack
(74) Attorney, Agent, or Firm—Dobrusin & Thennisch, PC

(57) ABSTRACT

A library of materials is screened for mechanical properties such as strength, tack or other properties. A library of materials is provided. A stimulus such as a stress or force is provided to each member of the library. A response (e.g., a strain) of each of the materials due to the stimulus is measured and the response, the stimulus or both are recorded and related to provide data. Thereafter, the data is analyzed to reach conclusions regarding properties of the material samples.

20 Claims, 5 Drawing Sheets

U.S. PATENT DOCUMENTS

| | | | |
|---|---|---|---|
| 4,789,236 A | 12/1988 | Hodor et al. |
| 4,793,174 A | 12/1988 | Yau |
| 4,829,837 A | 5/1989 | Telfer |
| 4,893,500 A | 1/1990 | Fink-Jensen |
| 4,899,575 A | 2/1990 | Chu et al. |
| 4,899,581 A | 2/1990 | Allen et al. |
| 4,932,270 A | 6/1990 | Lurie et al. |
| 4,975,320 A | 12/1990 | Goldstein et al. |
| 5,008,081 A | 4/1991 | Blau et al. |
| 5,051,239 A | 9/1991 | von der Goltz |
| 5,092,179 A | 3/1992 | Ferguson |
| 5,115,669 A | 5/1992 | Fuller et al. |
| 5,142,900 A | 9/1992 | Duke |
| 5,193,383 A | 3/1993 | Burnham et al. |
| 5,236,998 A | 8/1993 | Lundeen et al. |
| 5,269,190 A | 12/1993 | Kramer et al. |
| 5,271,266 A | 12/1993 | Eschbach |
| 5,272,912 A | 12/1993 | Katsuzaki |
| 5,280,717 A | 1/1994 | Hoseney et al. |
| 5,303,030 A | 4/1994 | Abraham et al. |
| 5,305,633 A | 4/1994 | Weissenbacher et al. |
| 5,398,885 A | 3/1995 | Andersson et al. |
| 5,437,192 A | 8/1995 | Kawamoto et al. |
| 5,438,863 A | 8/1995 | Johnson |
| 5,452,614 A | 9/1995 | Kato et al. |
| 5,452,619 A | 9/1995 | Kawanabe et al. |
| 5,481,153 A | 1/1996 | Turner |
| 5,517,860 A | 5/1996 | Lin et al. |
| 5,520,042 A | 5/1996 | Garritano et al. |
| 5,532,942 A | 7/1996 | Kitamura et al. |
| 5,610,325 A | 3/1997 | Rajagopal et al. |
| 5,626,779 A | 5/1997 | Okada |
| 5,699,159 A | 12/1997 | Mason |
| 5,700,953 A | 12/1997 | Hlady et al. |
| 5,723,792 A | 3/1998 | Miyazaki |
| 5,728,532 A | 3/1998 | Ackley |
| 5,756,883 A | 5/1998 | Forbes |
| 5,764,068 A | 6/1998 | Katz et al. |
| 5,776,359 A | 7/1998 | Schultz et al. |
| 5,817,947 A | 10/1998 | Bergerus |
| 5,821,407 A | 10/1998 | Sekiguchi et al. |
| 5,847,283 A | 12/1998 | Finot et al. |
| 5,877,428 A | 3/1999 | Scolton |
| 5,892,157 A | 4/1999 | Syre |
| 5,922,967 A | 7/1999 | Motoyama |
| 5,959,297 A | 9/1999 | Weinberg et al. |
| 5,985,356 A | 11/1999 | Schultz et al. |
| 5,999,887 A | 12/1999 | Giannakopoulos et al. |
| 6,004,617 A | 12/1999 | Schultz et al. |
| 6,010,616 A | 1/2000 | Lewis et al. |
| 6,013,199 A | 1/2000 | McFarland et al. |
| 6,030,917 A | 2/2000 | Weinberg et al. |
| 6,033,913 A | 3/2000 | Morozov et al. |
| 6,034,240 A | 3/2000 | La Pointe |
| 6,034,775 A | 3/2000 | McFarland et al. |
| 6,040,193 A | 3/2000 | Winkler et al. |
| 6,043,317 A | 3/2000 | Mumick et al. |
| 6,043,363 A | 3/2000 | LaPointe et al. |
| 6,045,671 A | 4/2000 | Wu et al. |
| 6,050,138 A | 4/2000 | Lynch et al. |
| 6,050,139 A | 4/2000 | Bousfield et al. |
| 6,087,181 A | 7/2000 | Cong |
| 6,092,414 A | 7/2000 | Newman |
| 6,124,476 A | 9/2000 | Guram et al. |
| 6,149,882 A | 11/2000 | Guan et al. |
| 6,151,123 A | 11/2000 | Nielsen |
| 6,157,449 A | 12/2000 | Hajduk |
| 6,175,409 B1 | 1/2001 | Nielsen et al. |
| 6,177,528 B1 | 1/2001 | LaPointe et al. |
| 6,182,499 B1 | 2/2001 | McFarland et al. |
| 6,187,164 B1 | 2/2001 | Warren et al. |
| 6,203,726 B1 | 3/2001 | Danielson et al. |
| 6,225,487 B1 | 5/2001 | Guram |
| 6,225,550 B1 | 5/2001 | Hornbostel et al. |
| 6,242,623 B1 | 6/2001 | Boussie et al. |
| 6,248,540 B1 | 6/2001 | Weinberg et al. |
| 6,260,407 B1 | 7/2001 | Petro et al. |
| 6,265,226 B1 | 7/2001 | Petro et al. |
| 6,265,601 B1 | 7/2001 | Guram et al. |
| 6,268,513 B1 | 7/2001 | Guram et al. |
| 6,294,388 B1 | 9/2001 | Petro |
| 6,296,771 B1 | 10/2001 | Miroslav |
| 6,306,658 B1 | 10/2001 | Turner et al. |
| 6,315,923 B1 | 11/2001 | Devenney et al. |
| 6,326,090 B1 | 12/2001 | Schultz et al. |
| 2002/0194930 A1 | 12/2002 | Crosby et al. |

OTHER PUBLICATIONS

The family of applications for U.S. Appl. No. 09/156,827 entitled "Formation of Combinatorial Arrays of Materials Using Solution–Based Methodologies" (Giaquinta et al.) filed Sep. 18, 1998.

The family of applications for U.S. Appl. No. 09/567,598 entitled "Polymer Libraries on a Substrate, Method for Forming Polymer Libraries on a Substrate and Characterization Methods with Same" (Boussie et al.) filed May 10, 2000.

U.S. Appl. No. 09/939,404 entitled "High Throughput Mechanical Property and Bulge Testing of Material Libraries," (D. Hajduk et al.) filed on Aug. 24, 2001.

U.S. Appl. No. 09/939,139 entitled "High Throughput Fabric Handle Screening," (M. Kossuth et al.) filed on Aug. 24, 2001.

U.S. Appl. No. 09/939,149 entitled "High Throughput Rheological Testing of Materials," (P. Mansky et al.) filed on Aug. 24, 2001.

U.S. Appl. No. 09/939,263 entitled "High Throughput Mechanical Property Testing of Materials Libraries Using Capacitance," (D. Haiduk et al.) filed on Aug. 24, 2001.

U.S. Appl. No. 09/938,994 entitled "High Throughput Mechanical Property Testing of Materials Libraries Using a Piezoelectric," (D. Hajduk) filed on Aug. 24, 2001.

The family of applications for U.S. Appl. No. 09/174,856 titled "Graphic Design of Combinatorial Material Libraries" (Lacy, et al.) filed on Oct. 19, 1998.

U.S. Appl. No. 09/801,165 entitled "Method and Apparatus for Characterizing Materials By Using a Mechanical Resonator" filed Mar. 7, 2001.

H.K. Chuang, C. Chiu and R. Paniagua, Avery Dennison, Pasadena, Calif. "Avery Adhesive Test Yields More Performance Data Than Traditional Probe" Adhesives Age Sep. 1997.

*Odian, Principles of Polymerization, 3rd Ed., John Wiley & Sons, Inc. (1991).

Young, W.C., Roark's Formulas for Stress and Stain, 1989.

*Timoshenko, S., Theory of Plates and Shells, McGraw–Hill, New York 1940.

Osterberg, Peter M. and Stephen D. Senturia, "M–Test: A Test Chip for MEMS Material Property Measurement Using Electrostatically Actuated Test Structures, " Journal of Microelecctromechanical Systems, vol. 6, No. 2, Jun. 1997.

Kim, J.O. and B. Lewis Slaten, "Objective Assessment of Fabric Handle in Fabrics Treated With Flame Retardants , " Journal of Testing and Evaluation, JTEVA, vol. 24, No. 4, Jul. 1996, pp. 223–228.

Grover, G. et al., "A Screening Technnique for Fabric Handle", J. Text. Inst., 1993, 84 No. J. Textile Institute, pp. 486–494.

Pan, Ning and K.C. Yen, "Physical Interpretations of Curves Obtained Through the Fabric Extraction Process for Handle Measurement, " Textile Research Journal 62(5), pp. 279–290.

"Handle–O–Meter", Thwing–Albert Instrument Company, Philadelphia, PA.

Raeel, Mastura and Jiang Liu, "An Empirical Model for Fabric Hand" Textile Research Journal 62, 1, pp. 31–38 (1991).

Ali, S.I. and Shahida Begum, "Fabric Softeners and Softness Perception", Ergonomics, v.37, No. 5, pp. 801–806 (1994).

"DMA 2980 Dynamic Mechanical Analyer, " http://www.tainst.com/dma2.html, Dec. 29, 2000.

"Introducing the NEW DMTA V?", http://www.rheometric-scientific.com/dmta V.htm, Dec. 29, 2000.

"Standard Test Method for Rubber Property–International Hardness, " American Society for Testing and Materials.

Amitay–Sadovsky, Ella and H. Daniel Wagner, "Evalution of Young's Modulus of Polymers from Knoop Microindentation Tests" Polymer Communications, 1998, vol. 39, No. 11, pp. 2387–2390.

Calleja, F.J. Balta, "Microhardness Studies of Polymers and Their Transtions" TRIP, Dec. 1994, vol. 2, No. 12, pp. 419–425.

Bowlt, C., "A Simple Capillary Viscometer" Physics Education, Mar. 1975, vol. 10, No. 2, pp. 102–103.

Lacombe, Robert H. and Jeremy Greenblatt, "Mechanical Properties of Thin Polyimide Films" pp. 647–668.

Shinozaki, D.M. and Y. Lu, "Micro–Indentation Relaxation Measuements in Polymer Thin Films" Journal of Electronic Materials, 1997, vol. 26, No. 7, pp. 852–858.

Wierenga, P.E. and A.J.J. Franken, "Ultramicroindentation Apparatus for the Mechanical Characterization of Thin Films" J. Appl. Phys., Jun. 15, 1984, 55 (12).

Europeans Search Report dated Dec. 10, 2001.

H.K. Chuang, C. Chiu and R. Paniagua, Avery Dennison, Pasadena, Calif. "Avery Adhesive Test Yields More Performance Data Than Traditional Probe" Adhesive Age Sep. 1997.

HIGH THROUGHPUT MECHANICAL RAPID SERIAL PROPERTY TESTING OF MATERIALS LIBRARIES

CLAIM OF PRIORITY

This application is a continuation of U.S. patent application Ser. No. 09/939,252, filed on Aug. 24, 2001 now abandoned.

TECHNICAL FIELD

The present invention generally relates to the field of materials characterization. In particular, the invention relates to high throughput rapid serial screens for evaluating properties such as, strength, tack, adhesiveness and the like of libraries of polymers or other materials.

BACKGROUND OF THE INVENTION

Currently, there is substantial research activity directed toward the discovery and optimization of polymeric materials for a wide range of applications. Although the chemistry of many polymers and polymerization reactions has been extensively studied, nonetheless, it is rarely possible to predict a priori the physical or chemical properties a particular polymeric material will possess or the precise composition and architecture that will result from any particular synthesis scheme. Thus, characterization techniques to determine such properties are an essential part of the discovery process.

Combinatorial chemistry refers generally to methods for synthesizing a collection of chemically diverse materials and to methods for rapidly testing or screening this collection of materials for desirable performance characteristics and properties. Combinatorial chemistry approaches have greatly improved the efficiency of discovery of useful materials. For example, material scientists have developed and applied combinatorial chemistry approaches to discover a variety of novel materials, including for example, high temperature superconductors, magnetoresistors, phosphors and catalysts. See, for example, U.S. Pat. No. 5,776,359 to Schultz et al. In comparison to traditional materials science research, combinatorial materials research can effectively evaluate much larger numbers of diverse compounds in a much shorter period of time. Although such high-throughput synthesis and screening methodologies are conceptually promising, substantial technical challenges exist for application thereof to specific research and commercial goals.

The characterization of polymers or other materials using combinatorial methods has only recently become known. Examples of such technology are disclosed, for example, in commonly owned U.S. Pat. Nos. 6,182,499 (McFarland et al); 6,175,409 B1 (Nielsen et al); 6,157,449 (Hajduk et al); 6,151,123 (Nielsen); 6,034,775 (McFarland et al); 5,959,297 (Weinberg et al), all of which are hereby expressly incorporated by reference herein.

Of particular interest to the present invention are combinatorial methods and apparatuses for synthesizing or otherwise providing polymers and other materials followed by screening of those materials for physical or mechanical characteristics such as strength, elasticity, tack, adhesiveness and the like. Synthesis and screening of the materials for mechanical properties presents a multitude of challenges. As an example, conventional instruments, such as conventional stress or strain testing machines and other instruments lack the ability to screen mechanical properties of several materials in rapid succession, in parallel, on a single substrate or a combination thereof. Thus, challenges are presented for building systems that can quickly process and test (either in parallel or in serial succession) mechanical properties of many materials. Additionally, challenges are presented for forming, processing or otherwise treating materials so that the materials are in appropriate condition for high throughput screening of mechanical properties.

SUMMARY OF THE INVENTION

In accordance with one preferred embodiment of the present invention, a method for screening an array of materials for strength is provided. According to the method a library of at least four sample materials is provided. One or more forces is applied to each of the at least four sample materials with one or more probes wherein the one or more probes are moved by an automatic system for applying the one or more forces. A sample response is monitored. Preferably, the response of each of the at least four sample materials is further correlated to assess strength (absolute, relative or both) of each of the at least four sample materials.

In accordance with another preferred embodiment of the present invention, a method for screening an array of materials for one or more adhesive properties is provided. According to the method a library of at least four sample materials is provided. Each of the at least four sample materials is contacted with at least one member for applying one or more forces to the at least four sample materials in opposition to the one or more adhesive properties of the at least four sample materials wherein the at least one member is moved by an automatic system for applying the one or more forces. A response is monitored. Preferably, the response of the each of the at least four sample materials is further correlated to assess the one or more adhesive properties of the each of the at least four sample materials.

In accordance with another preferred embodiment of the present invention, a method for measuring strength of a plurality of sample materials is provided. According to the method, a library comprising at least four different sample materials is provided. Thereafter, the strength of each of the at least four sample materials is measured at a throughput rate no greater than about 5 minutes per sample material.

In accordance with yet another preferred embodiment of the present invention, a method for measuring an adhesive property of a plurality of sample materials is provided. According to the method a library comprising at least four different sample materials is provided. Thereafter, the adhesive property of each of the at least four different sample materials is measured at a throughput rate no greater than about 5 minutes per sample material.

DETAILED DESCRIPTION OF THE PREFERRED EMBODIMENT

Glossary

Figure 1:
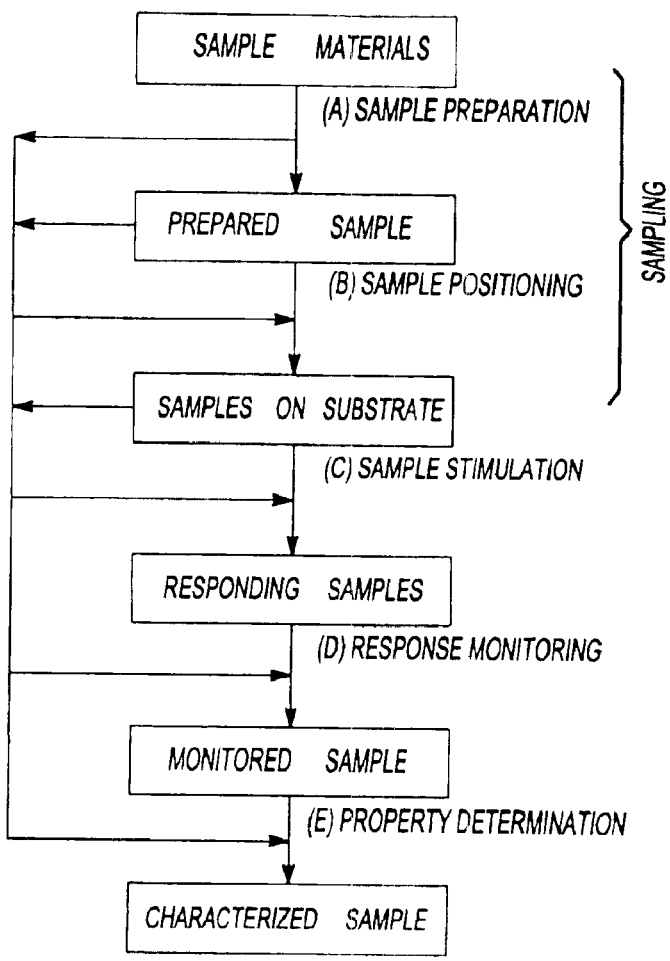
FIG. 1 is a flowchart of possible steps for methods of the present invention.

The following terms are intended to have the following general meanings as they are used herein.

Mixture: The term "mixture" refers to a collection of molecules, ions, electrons, chemical substances, etc. Each component in the mixture can be independently varied. A mixture can consist of two or more substances intermingled with no constant percentage composition, wherein each component may or may not retain its essential original properties, and where molecular phase mixing may or may not occur. In mixtures, the components making up the mixture may or may not remain distinguishable from each other by virtue of their chemical structure.

Adhesiveness or adhesive property: A measure of the tendency or ability of a material such as a sealant to adhesively secure itself or stick to one or more objects. The adhesiveness of a material may be due to bonding (chemical or otherwise) of the material to an object, electrostatic attraction of a material to an object or any other phenomenon that allows a material to secure itself to another object due at least in part to the natural characteristics or properties of the material. The term tack as used herein is considered to be an adhesive property. Also, as used herein, without limitation, adhesiveness may be defined by the deformation of an adhesive material due to a force applied against the adhesiveness of the material or by the amount of force acting against the adhesiveness of a material or by any other quantification that assists in defining the ability of a material to adhere itself to another object.

Strength: Generally strength, as used herein, relates to the ability of a material to resist a force, stress, strain or a combination thereof. Strength, as used herein, can mean any of these resistances and may be quantified or defined in terms of force, force per unit area, stress, strain and the like. Moreover, strength may be used generally to include any properties or quantifications related to the strength of a material. Examples of such properties or quantifications include, without limitation, moduli such as moduli of elasticity, young's modulus, shear modulus and the like, failure modes such as ultimate strength or other properties or quantifications related to strength.

These and other aspects of the invention are to be considered exemplary and non-limiting, and are discussed in greater detail below. The several aspects of the characterization methods and systems disclosed and claimed herein can be advantageously employed separately, or in combination to efficiently characterize a variety of materials, with particular emphasis on solid materials, polymeric materials, liquid materials or flowable materials. In preferred embodiments, these features are employed in combination to form a materials characterization system that can operate as a high-throughput screen in a combinatorial materials science research program directed to identifying and optimizing new materials. Such materials appropriate for combinatorial research may include, for instance, polymers, catalysts, products of various polymerization reaction conditions, lubricants, gels, adhesives, coatings and/or products of new post-synthesis processing conditions. Other materials appropriate for combinatorial research according to the present invention may include, but are not limited to, foodstuffs, cosmetics, beverages, lotions, creams, pharmaceuticals, inks, mucus, fuels, additives, detergents, surfactants, shampoos, conditioners, dyes, waxes, fuel cell electrolytes, photoresist, semiconductor material, wire coatings, hair styling products and the like.

Combinatorial Approaches for Science Research

In a combinatorial approach for identifying or optimizing materials or reactions, a large compositional space (e.g., in the context of polymers; of monomers, comonomers, catalysts, catalyst precursors, solvents, initiators, additives, or of relative ratios of two or more of the aforementioned) and/or a large reaction condition space (e.g., of temperature, pressure and reaction time) may be rapidly explored by preparing libraries and then rapidly screening such libraries. By way of illustration, polymer libraries can comprise, for example, polymerization product mixtures resulting from polymerization reactions that are varied with respect to such factors.

Combinatorial approaches for screening a polymer library can include an initial, primary screening, in which polymerization products are rapidly evaluated to provide valuable preliminary data and, optimally, to identify several "hits"—particular candidate materials having characteristics that meet or exceed certain predetermined metrics (e.g., performance characteristics, desirable properties, unexpected and/or unusual properties, etc.). Such metrics may be defined, for example, by the characteristics of a known or standard polymer or polymerization scheme. Because local performance maxima may exist in compositional spaces between those evaluated in the primary screening of the first libraries or alternatively, in process-condition spaces different from those considered in the first screening, it may be advantageous to screen more focused polymer libraries (e.g., libraries focused on a smaller range of compositional gradients, or libraries comprising compounds having incrementally smaller structural variations relative to those of the identified hits) and additionally or alternatively, subject the initial hits to variations in process conditions. Hence, a primary screen can be used reiteratively to explore localized and/or optimized compositional space in greater detail. The preparation and evaluation of more focused polymer libraries can continue as long as the high-throughput primary screen can meaningfully distinguish between neighboring library compositions or compounds.

Once one or more hits have been satisfactorily identified based on the primary screening, polymer and polymerization product libraries focused around the primary-screen hits can be evaluated with a secondary screen—a screen designed to provide (and typically verified, based on known materials, to provide) chemical composition or process conditions that relate with a greater degree of confidence to commercially-important processes and conditions than those applied in the primary screen. In many situations, such improved "real-world-modeling" considerations are incorporated into the secondary screen at the expense of methodology speed (e.g., as measured by sample throughput) compared to a corresponding primary screen. Particular polymer materials, catalysts, reactants, polymerization conditions or post-synthesis processing conditions having characteristics that surpass the predetermined metrics for the secondary screen may then be considered to be "leads." If desired, additional polymer or polymerization product libraries focused about such lead materials can be screened with additional secondary screens or with tertiary screens. Identified lead polymers, monomers, catalysts, catalyst precursors, initiators, additives or reaction conditions may be subsequently developed for commercial applications through traditional bench-scale and/or pilot scale experiments.

While the concept of primary screens and secondary screens as outlined above provides a valuable combinatorial research model for investigating polymers and polymerization reactions, a secondary screen may not be necessary for certain chemical processes where primary screens provide an adequate level of confidence as to scalability and/or where market conditions warrant a direct development approach. Similarly, where optimization of materials having known properties of interest is desired, it may be appropriate to start with a secondary screen. In general, the systems, devices and methods of the present invention may be applied as either a primary, secondary or other screen, depending on the specific research program and goals thereof. See, generally, U.S. patent application Ser. No. 09/227,558 entitled "Apparatus and Method of Research for Creating and Testing Novel Catalysts, Reactions and Polymers", filed Jan. 8, 1999 by Turner et al., for further discussion of a combinatorial approach to polymer science research. Bulk quantities of a particular material may be made after a primary screen, a secondary screen, or both.

According to the present invention, methods, systems and devices are disclosed that improve the efficiency and/or effectiveness of the steps necessary to characterize mechanical or physical properties of a material sample or a plurality of samples. In preferred embodiments, in the context of polymer analysis, a property of a plurality of polymer samples or of components thereof can be detected in a polymer characterization system with an average sample-throughput sufficient for an effective combinatorial polymer science research program.

Referring to FIG. 1, the systems and methods, preferably, start with a library or array of sample materials that may exhibit one or more predetermined physical/mechanical properties such as strength, tack, adhesiveness or the like. Ultimately, these predetermined properties will be determined in a determination step (Step E), however, several prior steps may be effected prior to Step E. The sample materials may be prepared such as by heating, cooling, or addition of additives. Such preparation is typically designed to affect the properties that are ultimately being determined. The sample materials may also be positioned in a desirable manner for property determination. The materials may be positioned on a substrate, a machine or otherwise positioned to assist in ultimately determining properties of the materials.

It will be appreciated that one of the advantageous features of the present invention is that it affords the ability to screen newly created materials some or all of which are uncharacterized or whose properties are unknown prior to the time of screening. Thus, previously unidentified and uncharacterized new materials can be screened for a common selected property. However, this does not prevent the employment of known references controls or standard as among the library members.

It shall be recognized that sample preparation (Step A) and sample positioning (Step B) may be optional steps in property determination protocols. Also sample preparation and sample positioning may be performed in any order if they are performed. Additionally it should be recognized that sequences other than the order of steps listed above are possible, and the above listing is not intended as limiting.

Typically, however, stimulation of the sample materials (Step C) is needed to effect one or more responses of the materials wherein the responses are related to the one or more physical properties that are being tested. Exemplary stimuli include force, contact, motion and the like. Exemplary responses include flow, or resistance to flow, deflection, adhesion, deformation, rupture or the like. Negative forces (e.g., compression as opposed to tension, negative pressure as opposed to positive pressure) or the like may be employed.

The responses of the materials are typically monitored (Step D) with hardware such as sensors, transducers, load cells or other like devices. Properties may be determined (Step E) quantitatively or qualitatively by relating the responses to the material properties.

A plurality of polymer samples may be characterized as described above in connection with FIG. 1. As a general approach for improving the sample throughput for a plurality of polymers, each of the steps (A) through (E) of FIG. 1 applicable to a given characterization protocol can be optimized with respect to time and quality of information, both individually and in combination with each other. Additionally or alternatively, each or some of such steps can be effected in a rapid-serial, parallel, serial-parallel or hybrid parallel-serial manner.

In preferred embodiments, a property such as tack, strength, adhesiveness or the like of a plurality of polymer samples or of components thereof can be analyzed in a polymer characterization system with an average sample-throughput sufficient for an effective combinatorial polymer science research program.

The throughput of a plurality of samples through a single step in a characterization process is improved by optimizing the speed of that step, while maintaining—to the extent necessary—the information-quality aspects of that step. Although conventional research norms, developed in the context in which research was rate-limited primarily by the synthesis of polymer samples, may find such an approach less than wholly satisfactory, the degree of rigor can be entirely satisfactory for a primary or a secondary screen of a combinatorial library of polymer samples. For combinatorial polymer research (and as well, for many on-line process control systems), the quality of information should be sufficiently rigorous to provide for scientifically acceptable distinctions between the compounds or process conditions being investigated, and for a secondary screen, to provide for scientifically acceptable correlation (e.g., values or, for some cases, trends) with more rigorous, albeit more laborious and time-consuming traditional characterization approaches.

The throughput of a plurality of samples through a series of steps, where such steps are repeated for the plurality of samples, can also be optimized. In one approach, one or more steps of the cycle can be compressed relative to traditional approaches or can have leading or lagging aspects truncated to allow other steps of the same cycle to occur sooner compared to the cycle with traditional approaches. In another approach, the earlier steps of a second cycle can be performed concurrently with the later steps of a first cycle. For example, in a rapid-serial approach for characterizing a sample, sample preparation, delivery to a substrate or the like, for a second sample in a series can be effected before or while the first sample in the series is being screened. As another example, a screen of a second sample in a series can be initiated while the first sample in the series is being screened.

A characterization protocol for a plurality of samples can involve a single-step process (e.g., direct measurement of a property of a sample or of a component thereof) or several steps. In a rapid-serial screen approach for a single-step process, the plurality of samples and a single measuring instrument or other instruments are serially positioned in relation to each other for serial analysis of the samples. In a parallel analysis approach, (e.g., as might be employed by itself, or in an upstream or downstream analysis of the samples relative to a rapid-serial analysis of the present invention) two or more measuring instruments or other apparatus are employed to measure properties of two or more samples simultaneously.

In a serial-parallel approach, a property of a larger number of samples (e.g., four or more) is screened as follows. First, a property of a subset of the four or more samples (e.g., 2 samples) is screened in parallel for the subset of samples, and then serially thereafter, a property of another subset of four or more samples is screened in parallel. It will be recognized, of course, that plural measuring instruments can be employed simultaneous, or plural measuring instruments can be employed serially.

For characterization protocols involving more than one step, optimization approaches to effect high-throughput characterization can vary. As one example, a plurality of samples can be characterized with a single characterization system (I) in a rapid-serial approach in which each of the plurality of samples ($s_1, s_2, s_3 \ldots s_n$) are processed serially through the characterization system (I) with each of the steps effected in series on each of the of samples to produce a serial stream of corresponding characterizing property information ($p_1, p_2, p_3 \ldots p_n$). This approach benefits from minimal capital investment, and may provide sufficient throughput—particularly when the steps have been optimized with respect to speed and quality of information.

As another example, a plurality of samples can be characterized with two or more instruments in a pure parallel (or for larger libraries, serial-parallel) approach in which the plurality of samples ($s_1, s_2, s_3 \ldots s_n$) or a subset thereof are processed through the two or more measurement systems (I, II, III . . . N) in parallel, with each individual system effecting each step on one of the samples to produce the property information ($p_1, p_2, p_3 \ldots p_n$) in parallel. This approach is advantageous with respect to overall throughput, but may be constrained by the required capital investment.

In a hybrid approach, certain of the steps of the characterization process can be effected in parallel, while certain other steps can be effected in series. Preferably, for example, it may be desirable to effect the longer, throughput-limiting steps in parallel for the plurality of samples, while effecting the faster, less limiting steps in series. Such a parallel-series hybrid approach can be exemplified by parallel sample preparation of a plurality of samples ($s_1, s_2, s_3 \ldots s_n$), followed by measuring with a single apparatus to produce a serial stream of corresponding characterizing property information ($P_1, p_2, p_3 \ldots p_n$). In another exemplary parallel-series hybrid approach, a plurality of samples ($s_1, s_2, s_3 \ldots s_n$) are prepared, measured and correlated in a slightly offset (staggered) parallel manner to produce the characterizing property information ($p_1, p_2, p_3 \ldots p_n$) in the same staggered-parallel manner.

Optimization of individual characterization steps with respect to speed and quality of information can improve sample throughput regardless of whether the overall characterization scheme involves a rapid-serial or parallel aspect (i.e., true parallel, serial-parallel or hybrid parallel-series approaches). As such, the optimization techniques disclosed hereinafter, while discussed primarily in the context of a rapid-serial approach, are not limited to such an approach, and will have application to schemes involving parallel characterization protocols that may be employed.

Sample Materials

The samples for which the present invention is useful for screening include polymeric materials or any other liquid, flowable or solid material that is capable of being provided as a liquid, solid, gel or other suitable form. Accordingly, without limitation, pure materials, mixtures of materials, bulk materials, particles of materials, thin films of materials, dispersions of materials, emulsions of materials, and solutions of materials are all contemplated as within the useful scope of the present invention.

In a particularly preferred embodiment, the present invention is employed for screening polymer samples, or plastic samples including polymers. Accordingly, unless otherwise stated, reference to screening of polymers or other processing of polymers includes plastics incorporating such polymers. The polymer sample can be a homogeneous polymer sample or a heterogeneous polymer sample, and in either case, comprises one or more polymer components. As used herein, the term "polymer component" refers to a sample component that includes one or more polymer molecules. The polymer molecules in a particular polymer component can have the same repeat unit, and can be structurally identical to each other or structurally different from each other. For example, a polymer component may comprise a number of different molecules, with each molecule having the same repeat unit, but with a number of molecules having different molecular weights from each other (e.g., due to a different degree of polymerization). As another example, a heterogeneous mixture of copolymer molecules may, in some cases, be included within a single polymer component (e.g., a copolymer with a regularly-occurring repeat unit), or may, in other cases, define two or more different polymer components (e.g., a copolymer with irregularly-occurring or randomly-occurring repeat units). Hence, different polymer components include polymer molecules having different repeat units. It is possible that a particular polymer sample (e.g., a member of a library) will not contain a particular polymer molecule or polymer component of interest.

In one embodiment, the polymer molecule of the polymer component is preferably, but need not be, a non-biological polymer. A non-biological polymer is, for purposes herein, a polymer other than an amino-acid polymer (e.g., protein) or a nucleic acid polymer (e.g., deoxyribonucleic acid (DNA)). However, the employment of the present invention for screening of materials for use as biological implants or prosthetics is contemplated. For instance, the ability of a biological polymer to bind to an agent may be determined from the mechanical property response of a sample of the material in the presence of such agent. The polymer molecule of the polymer component is, however, not generally critical; that is, the systems and methods disclosed herein will have broad application with respect to the type (e.g., architecture, composition, synthesis method or mechanism) and/or nature (e.g., physical state, form, attributes) of the polymer. Hence, the polymer molecule can be, with respect to homopolymer or copolymer architecture, a linear polymer, a branched polymer (e.g., short-chain branched, long-chained branched, hyper-branched), a cross-linked polymer, a cyclic polymer or a dendritic polymer. A copolymer molecule can be a random copolymer molecule, a block copolymer molecule (e.g., di-block, tri-block, multi-block, taper-block), a graft copolymer molecule or a comb copolymer molecule.

The particular composition of the polymer molecule is not critical. The material may be thermoplastic, thermoset or a mixture thereof. It may be a polycondensate, polyadduct, a modified natural polymer. Exemplary materials include polymers incorporating olefins, styrenes, acrylates, methacrylates, polyimides, polyamides, epoxies, silicones, phenolics, rubbers, halogenated polymers, polycarbonates, polyketones, urethanes, polyesters, silanes, sulfones, allyls, polyphenylene oxides, terphthalates, or mixtures thereof. Other specific illustrative examples can include repeat units or random occurrences of one or more of the following, without limitation: polyethylene, polypropylene, polystyrene, polyolefin, polyamide, polyimide, polyisobutylene, polyacrylonitrile, poly(vinyl chloride), poly(methyl methacrylate), poly(vinyl acetate), poly(vinylidene chloride), polytetrafluoroethylene, polyisoprene, polyacrylamide, polyacrylic acid, polyacrylate, poly(ethylene oxide), poly(ethyleneimine), polyamide, polyester, polyurethane, polysiloxane, polyether, polyphosphazine, polymethacrylate, and polyacetals. Polysaccharides are also preferably included within the scope of polymers. Exemplary naturally-occurring polysaccharides include cellulose, dextran, gums (e.g., guar gum, locust bean gum, tamarind xyloglucan, pullulan), and other naturally-occurring biomass. Exemplary semi-synthetic polysaccharides having industrial applications include cellulose diacetate, cellulose triacetate, acylated cellulose, carboxymethyl cellulose and hydroxypropyl cellulose. In any case, such naturally-occurring and semi-synthetic polysaccharides can be modified by reactions such as hydrolysis, esterification, alkylation, or by other reactions.

In typical applications, a polymer sample is a heterogeneous sample comprising one or more polymer components, one or more monomer components and/or and an additional phase which may be a continuous fluid phase. In copolymer applications, the polymer sample can comprise one or more copolymers, a first comonomer, a second comonomer, additional comonomers, and/or a continuous fluid phase. The polymer samples can, in any case, also include other components, such as catalysts, catalyst precursors (e.g., ligands, metal-precursors), solvents, initiators, additives, products of undesired side-reactions (e.g., polymer gel, or undesired homopolymer or copolymers) and/or impurities. Typical additives include, for example, surfactants, fillers, reinforcements, flame retardants, colorants, environmental protectants, other performance modifiers, control agents, plasticizers, cosolvents and/or accelerators, among others. In this regard, the present invention is particularly attractive for the screening of effects of variations of additives upon the characteristics of the material. The various components of the heterogeneous polymer sample can be uniformly or non-uniformly dispersed in the continuous fluid phase.

In one preferred embodiment, the polymer samples of the present invention are melted or otherwise heated to a fluid state, with the resulting material constituting a liquid sample. Heating may be performed simultaneously while the samples are on a common substrate. Alternatively, the samples might be heated to a liquid state and then transferred (e.g., manually or with an automated sampler) to a common substrate, where it is heated to maintain its liquid state. In yet another embodiment, the sample is heated to liquefy it or maintain its liquidity while being transferred to a common substrate (e.g., while in a probe of an automated sampler).

In another embodiment at a point prior to, during, or after depositing the sample onto the substrate, the polymer sample is preferably, chemically treated to form a liquid polymer sample, such as a polymer solution, a polymer emulsion, a polymer dispersion or a polymer that is liquid in the pure state (i.e., a neat polymer). A polymer solution comprises one or more polymer components dissolved in a solvent. The polymer solution can be of a form that includes well-dissolved chains and/or dissolved aggregated micelles. The solvent can vary, depending on the application, for example with respect to polarity, volatility, stability, and/or inertness or reactivity. Typical solvents include, for example, tetrahydrofuran (THF), toluene, hexane, ethers, trichlorobenzene, dichlorobenzene, dimethylformamide, water, aqueous buffers, alcohols, etc. According to traditional chemistry conventions, a polymer emulsion can be considered to comprise one or more liquid-phase polymer components emulsified (uniformly or non-uniformly) in a liquid continuous phase, and a polymer dispersion can be considered to comprise solid particles of one or more polymer components dispersed (uniformly or non-uniformly) in a liquid continuous phase. The polymer emulsion and the polymer dispersion can also be considered, however, to have the more typically employed meanings specific to the art of polymer science—of being a emulsion-polymerization product and dispersion-polymerization product, respectively. In such cases, for example, the emulsion polymer sample can more generally include one or more polymer components that are insoluble, but uniformly dispersed, in a continuous phase, with typical emulsions including polymer component particles ranging in diameter from about 1 nm to about 500 nm, more typically from about 5 nm to about 300 nm, and even more typically from about 40 nm to about 200 nm. The dispersion polymer sample can, in such cases, generally include polymer component particles that are dispersed (uniformly or nonuniformly) in a continuous phase, with typical particles having a diameter ranging from about 0.2 um to about 1000 um, more typically from about 0.4 um to about 500 um, and even more typically from about 0.5 um to about 200 um. Exemplary polymers that can be in the form of neat polymer samples include dendrimers, and siloxane, among others. The liquid polymer sample can also be employed in the form of a slurry, a latex, a microgel, a physical gel, or in any other form sufficient for creating an array for screening analysis as described and claimed herein. In some cases, polymer synthesis reactions (i.e., polymerizations) directly produce liquid samples. These may be bulk liquid polymers, polymer solutions, or heterogeneous liquid samples such as polymer emulsions, latices, or dispersions. In other cases, the polymer may be synthesized, stored or otherwise available for characterization in a non-liquid physical state, such as a solid state (e.g., crystalline, semicrystalline or amorphous), a glassy state or rubbery state. Hence, the polymer sample may need to be dissolved, dispersed or emulsified to form a liquid sample by addition of a continuous liquid-phase such as a solvent. The polymer sample can, regardless of its particular form, have various attributes, including variations with respect to polarity, solubility and/or miscibility.

In preferred applications, the polymer sample is a polymerization product mixture. As used herein, the term "polymerization product mixture" refers to a mixture of sample components obtained as a product from a polymerization reaction. An exemplary polymerization product mixture can be a sample from a combinatorial library prepared by polymerization reactions, or can be a polymer sample drawn off of an industrial process line. In general, the polymer sample may be obtained after the synthesis reaction is stopped or completed or during the course of the polymerization reaction. Alternatively, samples of each polymerization reaction can be taken and placed into an intermediate vessels at various times during the course of the synthesis, optionally with addition of more solvent or other reagents to arrest the synthesis reaction or prepare the samples for analysis. These intermediate samples can then be characterized at any time without interrupting the synthesis reaction.

It is also possible to use polymer samples or libraries of polymer samples that were prepared previously and stored. Typically, polymer libraries can be stored with agents to ensure polymer integrity. Such storage agents include, for example, antioxidants or other agents effective for preventing cross-linking of polymer molecules during storage. Depending upon the polymerization reaction, other processing steps may also be desired, all of which are preferably automated.

The polymerization scheme and/or mechanism by which the polymer molecules of the polymer component of the sample are prepared is not critical, and can include, for example, reactions considered to be addition polymerization, condensation polymerization, step-growth polymerization, and/or chain-growth polymerization reactions. Viewed from another aspect, the polymerization reaction can be an emulsion polymerization or a dispersion polymerization reaction. Viewed more specifically with respect to the mechanism, the polymerization reaction can be free radical polymerization, ionic polymerization (e.g., cationic polymerization, anionic polymerization), and/or ring-opening polymerization reactions, among others. Non-limiting examples of the foregoing include, Ziegler-Natta or Kaminsky-Sinn reactions and various copolymerization reactions. Polymerization product mixtures can also be prepared by modification of a polymeric starting materials, by grafting reactions, chain extension, chain scission, functional group interconversion, or other reactions.

It will be appreciated that in certain embodiments, a polymer sample is formed in situ on a substrate, post synthesis treated in situ on a substrate, or a combination thereof. Examples of such post synthesis treatment steps include for instance, heat treating, environmental exposure (e.g. temperature moisture, radiation, chemicals, etc.), aged, or the like.

In other preferred embodiments, polymer or other sample materials may be provided as solids or semi-solids. Such samples may be provided in a variety of geometric configurations such as blocks, cylinders, loops, films and the like. Generally, geometric configurations are selected to be appropriate for one or more tests that are to be performed upon the samples. Solid and semi-solid samples may be rigid, elastic, gelatinous or otherwise. In one preferred embodiment, samples are provided in a tacky state, and thus exhibits at least some degree of adhesiveness within the range of temperature under examination. Samples may also be specifically arranged for testing. For example, samples may be interwoven as a fabric, unwoven, machined to shape, molded to shape, cut to shape or otherwise physically manipulated for testing.

Sample Size

The sample size is not narrowly critical, and can generally vary, depending on the particular characterization protocols and systems used to analyze the sample or components thereof. However, it will be appreciated that the present invention advantageously permits for attaining reliable data with relatively small samples. Typical sample sizes can range from about 0.1 microgram to about 1 gram, more typically from about 1 microgram to about 100 milligrams, even more typically from about 5 micrograms to about 1000 micrograms, and still more typically from about 20 micrograms to about 50 micrograms.

If and when placed on a substrate for forming a library, as discussed herein with regard to sampling, the samples may be dispensed with any suitable dispensing apparatus (e.g. an automated micropipette or capillary dispenser, preferably with a heated tip). Each sample of the library is dispensed to an individually addressable region on the substrate. Preferably each sample occupies no more than about 1000 $mm^2$ of area on a substrate surface, more preferably no more than about 100 $mm^2$, and even more preferably no more than about 10 $mm^2$. In applications where the sample is disposed in a well, preferably the sample size does not exceed about 1000 milligrams.

Accordingly, for dispensing fluid samples, the individual samples are each dispensed in amounts no greater than about 100 ml, more preferably no greater than about 10 ml and still more preferably no greater than about 1 ml.

Libraries of Sample Materials

Libraries of samples have 2 or more samples that are physically or temporally separated from each other—for example, by residing in different regions of a common substrate, in different sample containers of a common substrate, by having a membrane or other partitioning material positioned between samples, or otherwise. The plurality of samples preferably has at least 4 samples and more at least 8 samples. Four samples can be employed, for example, in connection with experiments having one control sample and three polymer samples varying (e.g., with respect to composition or process conditions as discussed above) to be representative of a high, a medium and a low-value of the varied factor—and thereby, to provide some indication as to trends. Four samples are also a minimum number of samples to effect a serial-parallel characterization approach, as described above (e.g., with two analytical instruments operating in parallel). Eight samples can provide for additional variations in the explored factor space. Moreover, eight samples corresponds to the number of parallel polymerization reactors in the PPR-8™, being selectively offered as one of the Discovery Tools™ of Symyx Technologies, Inc. (Santa Clara, Calif.), which can be used to prepare polymers for screening in accordance with the present invention. Higher numbers of samples can be investigated, according to the methods of the invention, to provide additional insights into larger compositional and/or process space. In some cases, for example, the plurality of samples can be 15 or more samples, preferably 20 or more samples, more preferably 40 or more samples and even more preferably 80 or more samples. Such numbers can be loosely associated with standard configurations of other parallel reactor configurations for synthesizing materials for screening herein (e.g., the PPR-48™, Symyx Technologies, Inc.) or of standard sample containers (e.g., 96-well microtiter plate-type formats). Moreover, even larger numbers of samples can be characterized according to the methods of the present invention for larger scale research endeavors. Hence, for screening of polymers or other materials the number of samples can be 150 or more, 400 or more, 500 or more, 750 or more, 1,000 or more, 1,500 or more, 2,000 or more, 5,000 or more and 10,000 or more samples. As such, the number of samples can range from about 2 samples to about 10,000 samples or more, and preferably from about 8 samples to about 10,000 or more samples. In many applications, however, the number of samples can range from about 80 samples to about 1500 samples.

In some cases, in which processing of samples using typical 96-well microtiter-plate formatting or scaling is convenient or otherwise desirable, the number of samples can be 96*N, where N is an integer ranging from about 1 to about 100 or greater. For many applications, N can suitably range from 1 to about 20, and in some cases, from 1 to about 5.

A library of samples comprises two or more different samples spatially separated—preferably, but not necessarily on a common substrate, or temporally separated. Candidate samples (i.e., members) within a library may differ in a definable and typically predefined way, including with regard to chemical structure, processing (e.g., synthesis) history, mixtures of interacting components, post-synthesis treatment, purity, etc. The samples are spatially separated, preferably at an exposed surface of the substrate, such that the library of samples is separately addressable for characterization thereof. The two or more different samples can reside in sample containers formed as wells in a surface of the substrate. The number of samples included within the library can generally be the same as the number of samples included within the plurality of samples, as discussed above. In general, however, not all of the samples within a library of samples need to be different samples. When process conditions are to be evaluated, the libraries may contain only one type of sample. The use of reference standards, controls or calibration standards may also be performed, though it is not necessary. Further, a library may be defined to include sub-groups of members of different libraries, or it may include combinations of plural libraries.

Typically, however, for combinatorial science research applications, at least two or more, preferably at least four or more, even more preferably eight or more and, in many cases, most preferably each of the plurality of polymer samples in a given library of samples will be different from each other. Specifically, a different sample can be included within at least about 50%, preferably at least 75%, preferably at least 80%, even more preferably at least 90%, still more preferably at least 95%, yet more preferably at least 98% and most preferably at least 99% of the samples included in the sample library. In some cases, all of the samples in a library of samples will be different from each other.

In one embodiment, preferably at least eight samples are provided in a library on a substrate and at least about 50% of the samples included in the library are different from each other. More preferably, the library includes at least 16 samples and at least 75% of said samples included in said library are different from each other. Still more preferably, the library includes at least 48 samples and at least 90% of said samples included in the library are different from each other.

The substrate can be a structure having a rigid or semi-rigid surface on which or into which the library of samples can be formed, mounted, deposited or otherwise positioned. The substrate can be of any suitable material, and preferably includes materials that are inert with respect to the polymer samples of interest, or otherwise will not materially affect the mechanical or physical characteristics of one sample in an array relative to another. Organic and inorganic polymers may also be suitably employed in some applications of the invention. Exemplary polymeric materials that can be suitable as a substrate material in particular applications include polyimides such as Kapton™., polypropylene, polytetrafluoroethylene (PTFE) and/or polyether etherketone (PEEK), among others. The substrate material is also preferably selected for suitability in connection with known fabrication techniques. Metal or ceramic (e.g., stainless steel, silicon, including polycrystalline silicon, single-crystal silicon, sputtered silicon, and silica ($SiO_2$) in any of its forms (quartz, glass, etc.)) are also preferred substrate materials. Other known materials (e.g., silicon nitride, silicon carbide, metal oxides (e.g., alumina), mixed metal oxides, metal halides (e.g., magnesium chloride), minerals, zeolites, and ceramics) may also be suitable for a substrate material in some applications. As to form, the sample containers formed in, at or on a substrate can be preferably, but are not necessarily, arranged in a substantially flat, substantially planar surface of the substrate. The sample containers can be formed in a surface of the substrate as dimples, spots, wells, raised regions, trenches, or the like. Non-conventional substrate-based sample containers, such as relatively flat surfaces having surface-modified regions (e.g., selectively wettable regions) can also be employed. The overall size and/or shape of the substrate is not limiting to the invention. The size and shape can be chosen, however, to be compatible with commercial availability, existing fabrication techniques, and/or with known or later-developed automation techniques, including automated sampling and automated substrate-handling devices. The substrate is also preferably sized to be portable by humans. The substrate can be thermally insulated, particularly for high-temperature and/or low-temperature applications.

In certain preferred embodiments, the substrate is formed to securely maintain contact with a plurality of samples. According to various methodologies it may be desirable to place forces on samples while the samples remain secured to the substrate. Forces may be applied to the samples by one or more members separate from the substrate or the substrate may apply the forces.

In one particularly preferred embodiment, the library includes a combinatorial library of polymerization product mixtures. Polymer libraries can comprise, for example, polymerization product mixtures resulting from polymerization reactions that are varied with respect to, for example, reactant materials (e.g., monomers, comonomers), catalysts, catalyst precursors, initiators, additives, the relative amounts of such components, reaction conditions (e.g., temperature, pressure, reaction time), post-synthesis treatment, or any other factor affecting polymerization or material properties. Design variables for polymerization reactions are well known in the art. See generally, Odian, Principles of Polymerization, 3rd Ed., John Wiley & Sons, Inc. (1991). A library of polymer samples may be prepared in parallel polymerization reactors or in a serial fashion. Exemplary methods and apparatus for preparing polymer libraries—based on combinatorial polymer synthesis approaches—are disclosed in copending U.S. patent application Ser. No. 09/211,982 of Turner et al. filed Dec. 14, 1998, copending U.S. patent application Ser. No. 09/227,558 of Turner et al. filed Jan. 8, 1999, copending U.S. patent application Ser. No. 09/235,368 of Weinberg et al. filed Jan. 21, 1999, and copending U.S. provisional patent application Ser. No. 60/122,704 entitled "Controlled, Stable Free Radical Emulsion and Water-Based Polymerizations", filed Mar. 9, 1999 by Klaemer et al. See also, PCT Pat. Application WO 96/11878.

Non-Polymer Sample Materials

Although several of the primary applications of the present invention are directed to combinatorial polymer science research and/or quality control for industrial polymer synthesis or processing protocols, some aspects of the invention can have applications involving non-polymer samples. A non-polymer sample can be a material that comprises an organic or an inorganic non-polymer element or compound. For purposes herein, oligomers are considered to be polymers rather than non-polymers. The non-polymer molecule is, in some cases, preferably a non-biological non-polymer element or compound. Such non-biological non-polymer elements or compounds include non-polymer elements or compounds other than those having a well-characterized biological activity and/or a primary commercial application for a biological field (e.g., steroids, hormones, etc.). More particularly, such non-biological, non-polymer elements or compounds can include organic or inorganic pigments, carbon powders (e.g., carbon black), metals, metal compounds, metal oxides, metal salts, metal colloids, metal ligands, etc, without particular limitation. Other materials, which may be characterized according to the present invention include, without limitation, ceramic materials, semiconducting and conducting materials, metals and composites. Still other materials for which the present application finds utility are discussed elsewhere herein.

Sampling/Auto-Sampler

Sampling of sample materials may be accomplished with a plurality of steps, which include withdrawing a sample from a sample container and delivering at least a portion of the withdrawn sample to a substrate such as a microtiter plate. Sampling may also include additional steps, particularly and preferably, sample preparation steps. In one approach, only one sample is withdrawn into the auto-sampler probe at a time and only one sample resides in the probe at one time. In other embodiments, multiple samples may be drawn into the auto-sampler probe separated by solvents. In still other embodiments, multiple probes may be used in parallel for auto sampling.

In the general case, sampling can be effected manually, in a semi-automatic manner or in an automatic manner. A sample can be withdrawn from a sample container manually, for example, with a pipette or with a syringe-type manual probe, and then manually delivered to a loading port or an injection port of a characterization system. In a semi-automatic protocol, some aspect of the protocol is effected automatically (e.g., delivery), but some other aspect requires manual intervention (e.g., withdrawal of samples from a process control line). Preferably, however, the sample(s) are withdrawn from a sample container and delivered to the characterization system in a fully automated manner—for example, with an auto-sampler.

In one embodiment, auto-sampling may be done using a microprocessor controlling an automated system (e.g., a robot arm). Preferably, the microprocessor is user-programmable to accommodate libraries of samples having varying arrangements of samples (e.g., square arrays with "n-rows" by "n-columns", rectangular arrays with "n-rows" by "m-columns", round arrays, triangular arrays with "r-" by "r-" by "r-" equilateral sides, triangular arrays with "r-base" by "s-" by "s-" isosceles sides, etc., where n, m, r, and s are integers).

Automated sampling of sample materials optionally may be effected with an auto-sampler having a heated injection probe (tip). An example of one such auto sampler is disclosed in U.S. Pat. No. 6,175,409 B1 (incorporated by reference).

Analytical Systems and Methods

According to the present invention, one or more systems, methods or both are used to determine the mechanical properties of a plurality of sample materials. Though manual or semi-automated systems and methods are possible, preferably an automated system or method is employed. A variety of robotic or automatic systems are available for automatically or programmably providing predetermined motions for handling, contacting, dispensing, or otherwise manipulating materials in solid, fluid liquid or gas form according to a predetermined protocol. Such systems may be adapted or augmented to include a variety of hardware, software or both to assist the systems in determining mechanical properties of materials. Hardware and software for augmenting the robotic systems may include, but are not limited to, sensors, transducers, data acquisition and manipulation hardware, data acquisition and manipulation software and the like. Exemplary robotic systems are commercially available from CAVRO Scientific Instruments (e.g., Model NO. RSP9652) or BioDot (Microdrop Model 3000).

Figure 2:
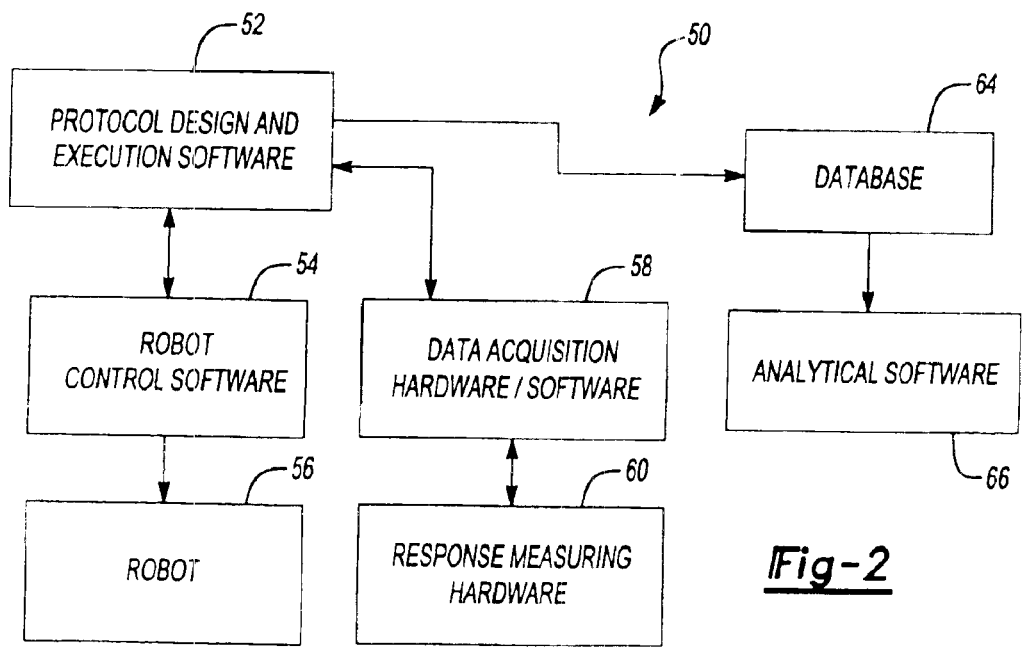
FIG. 2 is a block diagram of a potential platform system for executing methods and for operating systems of the present invention.

Referring to FIG. 2, there is a flow schematic diagram of an exemplary automated system 50 for rapid determination of mechanical properties of several samples of material. Generally, the system 50 includes a suitable protocol design and execution software 52 that can be programmed with information such as synthesis, composition, location information or other information related to a library of materials positioned with respect to a substrate. The protocol design and execution software is typically in communication with robot control software 54 for controlling a robot 56 or other automated apparatus or system. The protocol design and execution software 52 is also in communication with data acquisition hardware/software 58 for collecting data from response measuring hardware 60. Preferably, the robot control software 54 commands the robot 56 to apply stimuli to sample materials to evoke a response from the materials. At substantially the same time, the response measuring hardware 60 (e.g., sensors, transducers, load cells and the like) monitors the responses of the materials, the stimuli being applied to the materials or both and provides data on the responses to the data acquisition hardware/software 58. Thereafter, the robot control software 54, the data acquisition hardware/software 58 or both transmit data to the protocol design and execution software 52 such that the sample materials or information about the sample materials may be matched with their responses to the applied stimuli and transmitted at data to a database 64. Once the data is collected in the database, analytical software 66 may be used to analyze the data, and more specifically, to determine mechanical properties of the sample materials, or the data may be analyzed manually.

In a preferred embodiment, the system is driven by suitable software, such as LIBRARY STUDIO™, by Symyx Technologies, Inc. (Santa Clara, Calif.); IMPRESSIONIST™, by Symyx Technologies, Inc. (Santa Clara, Calif.); EPOCH™, by Symyx Technologies, Inc. (Santa Clara, Calif.) or a combination thereof. Moreover, data collected or produced by the system may be viewed using other suitable software such as POLYVIEW™, by Symyx Technologies, Inc. (Santa Clara, Calif.). The skilled artisan will appreciate that the above-listed software can be adapted for use in the present invention, taking into account the disclosures set forth in commonly-owned and copending U.S. patent application Ser. No. 09/174,856 filed on Oct. 19, 1998, U.S. patent application Ser. No. 09/305,830 filed on May 5, 1999 and WO 00/67086, U.S. patent application Ser. No. 09/420,334 filed on Oct. 18, 1999, U.S. patent application Ser. No. 09/550,549 filed on Apr. 14, 2000, each of which is hereby incorporated by reference. Additionally, the system may also use a database system developed by Symyx Technologies, Inc. to store and retrieve data with the overlays such as those disclosed in commonly-owned and copending U.S. patent application Ser. No. 09/755,623 filed on Jan. 5, 2001, which is hereby incorporated by reference for all purposes. The software preferably provides graphical user interfaces to permit users to design libraries of materials by permitting the input of data concerning the precise location on a substrate of a material (i.e., the address of the material). Upon entry, the software will execute commands to control movement of the robot, for controlling activity at such individual address.

Figure 6:
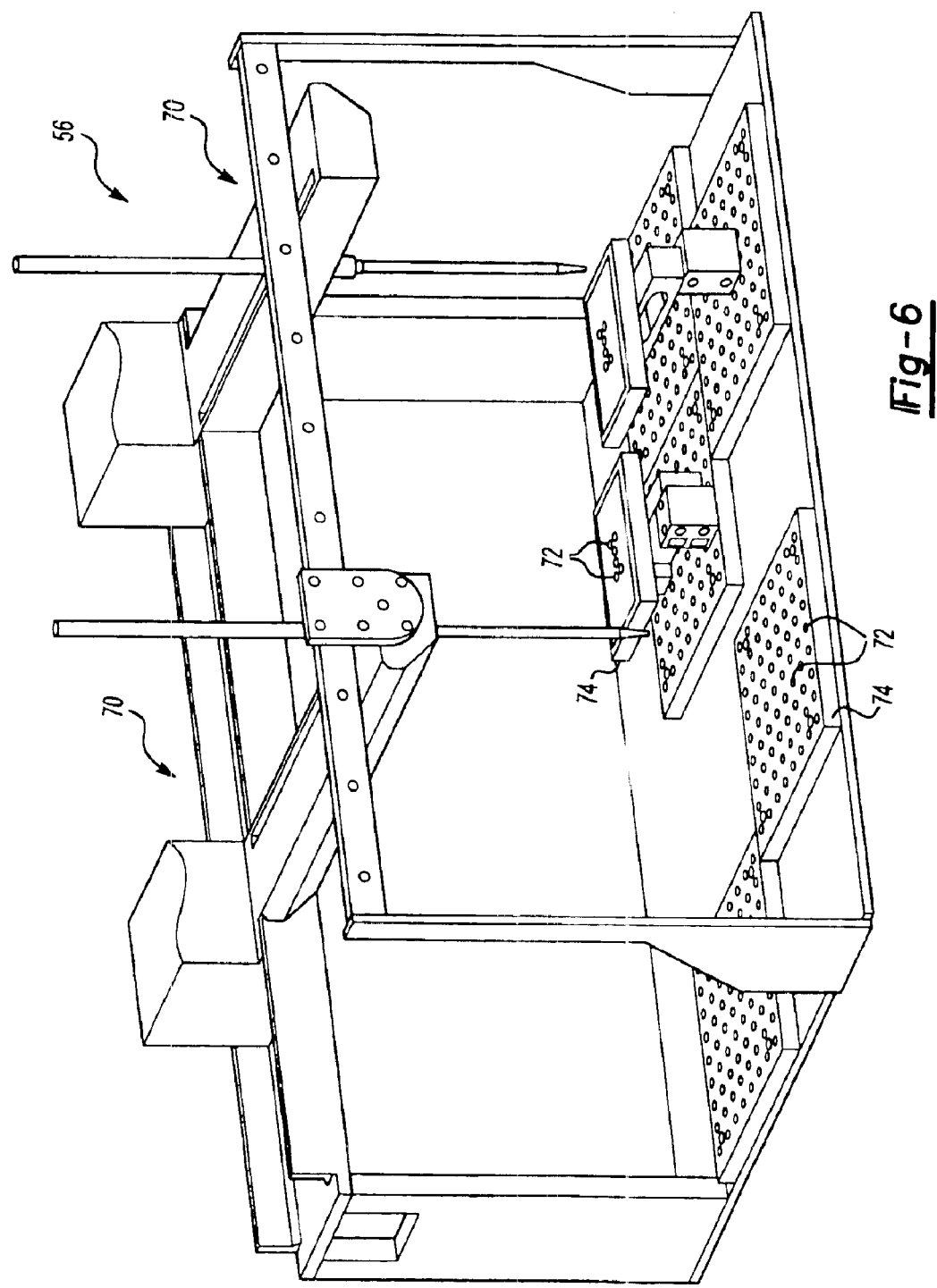
FIG. 6 is an exemplary automated apparatus or system for assisting in determining mechanical properties in accordance with the present invention.

In FIG. 6, there is illustrated one exemplary automated robot or apparatus 56 that may be operated using the system

50 of FIG. 2. As shown in FIG. 6, the apparatus 56 includes a pair of robot arms 70 appropriate for manipulating sample materials 72 located upon substrates 74.

Many of such aspects of the invention can be directly translated for use with parallel, serial or serial-parallel protocols. In a most preferred embodiment, for example, a rapid serial force system and protocols for that system can be used for characterization of materials with very high sample throughput.

Mechanical Strength Analysis

The system and method of the present invention may determine mechanical strength or collect information related to the mechanical strength of individual members of one or more libraries of materials. As used herein, a determination of strength of a material should be construed as including determinations of strength itself and determinations of responses such as deformations of sample materials that are related to strength. According to one embodiment a stimulus such as a force (e.g., stress) is applied, either manually or automatically, to each member of the array of materials using a probe, an actuator or other device. As the stimulus is applied the response of the materials due to the stimulus is monitored using a transducer (e.g., a sensor). Thereafter, one or more strengths of each of the materials in the array are determined based upon the response exhibited by the materials and based upon predetermined factors such as the geometry of the material samples, the geometry or configuration of the probe that provides the stimulation and the like.

Generally, the stimulus will be a force that is applied to the materials. The force applied to the material may be any suitable force such as tensile, compressive, torsional, shear, expansive or a combination thereof. The forces may be continuous, variable, intermittent, vibratory, repetitive or otherwise. The forces may be applied, recorded or both as a function of time. The forces may be applied with one of the robots or automated systems previously discussed or by another suitable robot or machine. The force may be applied by direct contact of a sample with a solid, such as with a probe, or through the direction of a fluid toward or away from the sample. For example, sample materials may be placed in a pressurized liquid or gas to compress the materials so that compressive strength of the material may be determined. They may be placed in a sealed chamber and a vacuum or other negative pressure applied. Alternatively, sample materials may be physically attached to two or more members wherein at least one of the members is moveable toward or away from another member to respectively exert compressive or tensile force upon the materials.

In other alternative embodiments, each member of the array of materials may be attached to one or more substrates and a robot or other automated system may exert forces upon the materials while the materials remain attached to the substrate. In that case, the transducer (e.g., a load cell) may be attached to the substrate such that the force applied to each sample material may be measured as it is applied to the entire substrate. Alternatively or additionally, a transducer (e.g., a load cell or displacement measurement device) may be attached to one or more probes and the probe[s] may measure the force applied to each sample on the substrate or the response of each sample on the substrate. Moreover, each of the material samples may be attached to or supported by its own portion (e.g., a chip, block or the like) of the substrate and the substrate may include a transducer corresponding to each portion of the substrate for individually measuring force applied to material samples or for individually measuring the response of the material samples.

The forces may be predetermined or may be measured or monitored as they are applied. The forces may be applied using one or more than one member or device for exerting one or more than one force on each sample. Alternatively, one member or device may exert one or more forces on a plurality of samples. The forces may be applied by moving sample materials relative to a probe, by moving a probe relative to the sample materials or a combination thereof. Moreover, individual material samples or groups of samples may be sequentially transported in vials, on other substrates or alone to a location adjacent the probe, the actuator, the transducer or the like for performing measurements on the material samples.

Other suitable forces may be employed as well, including but not limited to those obtainable electrically, electromagnetically, piezoelectrically, magnetically, thermally or the like.

A variety of transducers such as sensors, load cells and the like may be used within the systems for monitoring and/or measuring the forces being applied to the materials, the strains of the materials or both. Load cells may be used for monitoring forces being applied to materials. The loads cell may be attached to or contacting the robots, automated systems, substrates, materials being tested or a combination thereof. A multitude of sensors such as resistive, optical, visual, x-ray diffractive or other suitable sensors may be used to monitor strain or deformation of materials resulting from forces exerted on those materials. Alternatively, sensors having members that moveably contact the materials, substrates, automated systems or combinations thereof to assist in monitoring strains of materials may be used. One or more transducers or sensors may be used to monitor each sample. Alternatively, sensors may be used to monitor a plurality of samples. Thus, depending upon the transducer used, a strain of a material may be measured as the strain is induced by a predetermined force, a force may be measured as a predetermined strain is induced in the sample or a force and a strain of a sample may be measured together for each sample material.

The strains of the materials that are measured may involve compression, elongation, deflection, torsion, expansion or shearing of the materials. The strains of the materials may be elastic, plastic or may deform the materials to failure. Additionally, the materials may be deformed in one, or more than one direction.

In addition to measuring strains of the sample materials, other responses of sample materials may be measured as well. As an example, a sample material of an original predetermined configuration may be subjected to a force that causes a predetermined deformation or strain of the sample material. Once the predetermined deformation or strain has been achieved, the force needed to cause the deformation or strain and/or the force exhibited by the sample material in an effort to return to its original predetermined configuration may be measured and/or monitored. Then, the monitored or measured forces may be correlated to the deformation or strain of the sample material and to the dimensions of the original predetermined configuration of the sample material for determining strength of the sample material.

As an example, strengths of the materials may generally be determined by relating the strains of the materials to the force per unit area applied to the materials. The system and method may be designed to determine elastic strengths, yield strengths, ultimate strengths, fracture strengths, fatigue strengths, the strengths of a material for predetermined forces applied to the materials or other suitable strengths. Flexural, Elasticity of other Moduli may be measured, calculated, or otherwise used to assist in determining strengths of materials. In a preferred embodiment, the materials may be formed to have a portion with a smaller predetermined cross-sectional area that is expected to fail when force is applied to the material. Then, the cross-sectional area and the force used to cause failure can be used to determine the strength of the material.

Figure 3:
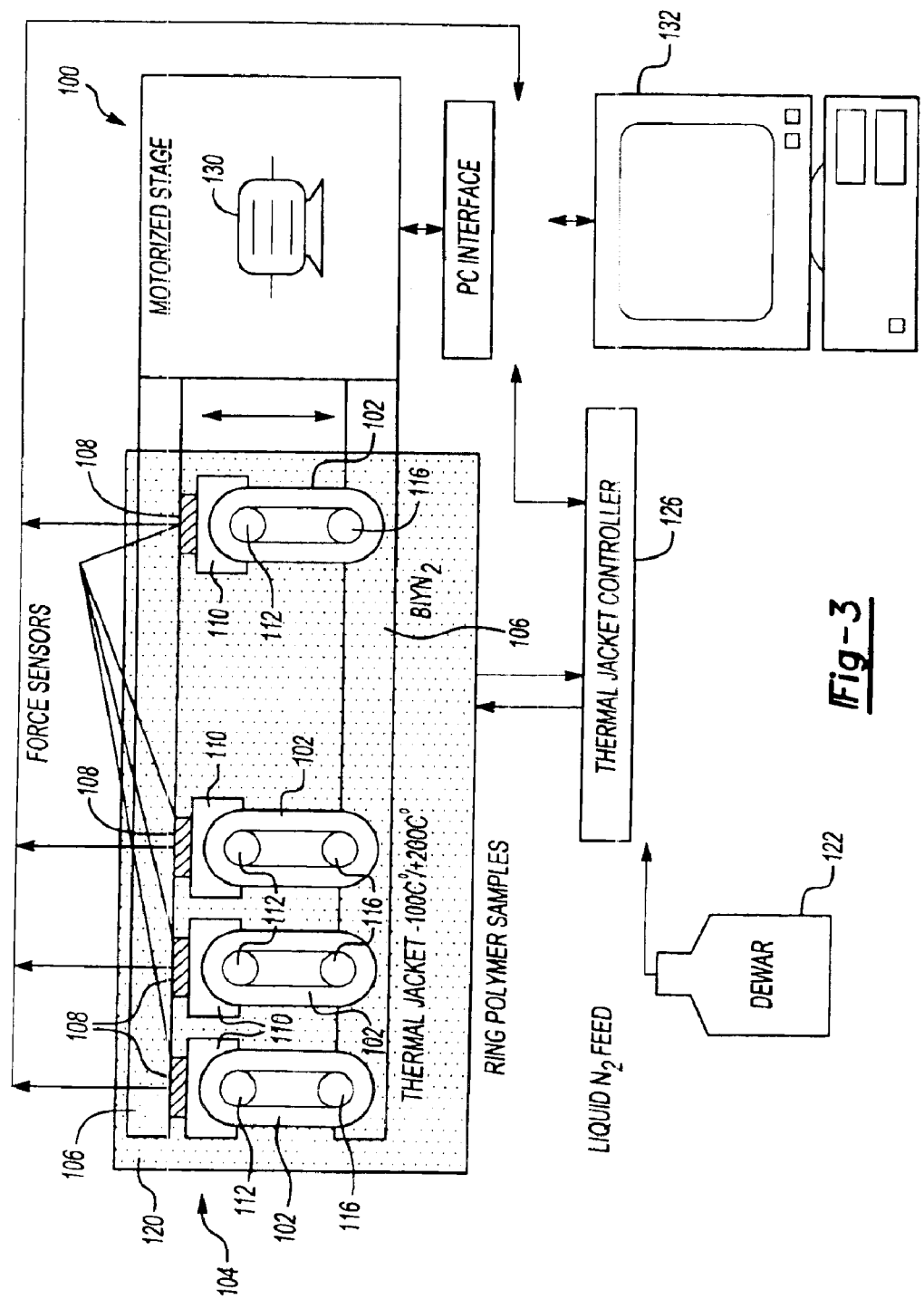
FIG. 3 is a schematic of a system for assisting in determining mechanical properties of materials in accordance with the present invention.

Referring to FIG. 3, there is illustrated one embodiment of a system 100 for measuring mechanical strength of a library of sample materials 102. The system 100 includes a substrate 104 having a pair of opposing jaw members 106. One of the jaw members 106 is associated with a plurality of force sensors 108, which may be attached to one or more suitable sample mounting blocsk 110. Each block 110 including a pin or other like device for engaging a test specimen 112. The other opposed member 106 includes several pins 116 corresponding to and opposing the pins 112 of the blocks 110. In the present embodiment, the sample materials 102 are preferably provided in a solid state. For example as shown, they are configured as loops 102 and are looped about one attachment member 112 (e.g. a pin) attached to the one of the opposing members 106 and another opposing attachment member (e.g. pin) 116 attached to the other opposing jaw 106. The loops 102 may range in size and thickness. For example, thicknesses of cross-sections of the loops 102 may range from 0.1 mm to 10 mm and more preferably from about 1 mm to about 3 mm. Moreover, the size of the loops (i.e., a distance defined as a circumference or outer perimeter of the loop) may range from about 10 mm to about 1000 mm and more preferably from about 50 mm to about 500 mm.

Optionally, as shown in FIG. 3, the system 100 further includes a suitable apparatus, such as a thermal jacket 120 for heating and cooling the materials 102. One preferred thermal jacket 120 includes passages (not shown) for receiving a heated or cooled fluid such as liquid nitrogen, water, steam or other suitable fluid from a fluid supply 122. The fluid from the fluid supply 122 may be pumped to the thermal jacket 120 with a pump (not shown) that is controlled by a controller 126.

In operation, the material samples 102 are loaded onto the pins 112, 116, the materials 102 are heated or cooled as desired (e.g., preferably between—100° C. and 200° C.) by the thermal jacket 120, and the opposing members 106 are moved toward or moved away from each other such that the pins 112, 116 place a force upon the materials 102. The amount of force being applied to each material 102 is being monitored by the force sensors 108. Preferably, the opposing jaws 114 are moved relative to each other using a suitable actuator, such as a motor 130 or otherwise. As can be seen one or more computerized systems 132 may be used to control the conditions for testing, such as the heating and cooling of the materials 102, the rate at which the opposing jaws 106 move relative to each other and the forces being applied to each of the materials 102.

Figure 4:
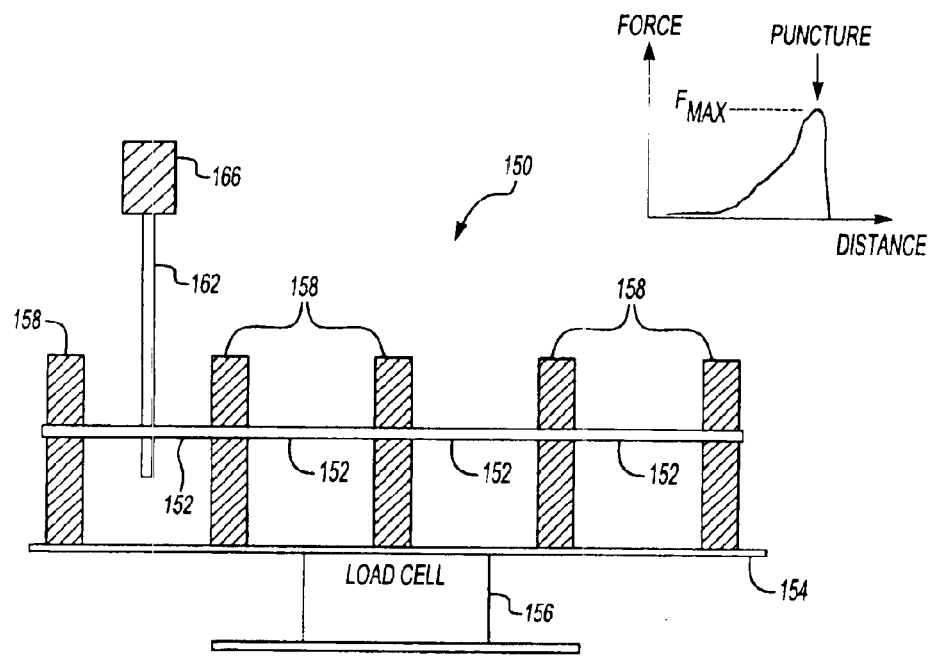
FIG. 4 is a schematic of a system for assisting in determining mechanical properties of materials in accordance with the present invention.

Referring to FIG. 4, there is illustrated another alternative system 150 for measuring strengths of sample materials 152. As shown, the system 150 includes a substrate 154 mounted atop at least one load cell 156. The substrate 154 includes a plurality of spaced apart support members 158. A plurality of sample materials 152 are attached to one or more of the support members 158. Preferably, each of the sample materials 152 is a sheet (e.g. a single layer or multi player film, a coated or uncoated substrate or foil, a woven or unwoven fabric, or the like). The sheet may be spanned and secured at the ends of each sample or about the periphery of each sample, such as by opposing support members 158. The system also includes a probe 162 for placing a force upon each of the materials 152. Preferably, the probe 162 is attached to a robot or other automated system (not shown) with a spring 166 for placing a force upon each of the sample materials 152 until the sample material 152 fails (e.g., rupture, rips, punctures, tears or otherwise). As the probe 162 applies a force (e.g. by pushing or pulling the sample) to the sample materials 152 the load cell 156 measures the amount of force being applied such that the failure strength (i.e., the amount of force or stress required to make the materials 152 fail) of each of the materials 152 may be determined. Advantageously, the spring 166 provides a cushion to the amount of force being applied by the probe 162 such that the force may be more accurately monitored. It may also be advantageous to provide more than one load cell to support and balance the substrate 154 such that forces applied to the materials 152 are measured rather than torques or moments. Shear may also be measured, for instance, by notching the sample and measuring growth of the notch In response to the probe force.

It will be appreciated that any of a number of additional stimuli may be introduced and the effects of which analyzed. For example, cyclical loading with a suitable motor can be employed for addressing fatigue strength of each sample. Additionally, various environmental conditions such as humidity, temperature, pressure and the like may be altered (e.g., raised or lowered) around the sample materials to vary tests of the sample materials.

Tack or Adhesive Measurements

The system and method of the present invention may also determine adhesive properties such as tack, shear and the like for each member of an array of materials. As used herein, the term adhesive and it conjugations should be construed as including adhesive strength and all of the properties or quantifications related to adhesion. According to one embodiment of the invention, a stimulus such as a force is applied to each of the materials with a member. The force is applied to oppose adhesive forces of the materials that try to maintain a connection with the member or a substrate to which the materials are adhesively secured. During application of the forces responses of the materials are monitored and the responses are used to determine the adhesiveness or tack of each of the materials.

Preferably, each member of the library of materials includes a surface that is flat, curved, contoured or is otherwise adapted for adhesively contacting a corresponding surface of a member (e.g., a probe). Thereafter, the member is moved at least partially away from the surface of the materials to apply a force in opposition to tack or adhesive forces of the materials. The force applied to the materials may be tensile, compressive, shear or a combination thereof. The force may be continuous, intermittent, vibratory, repetitive or otherwise. The force may be applied with one of the robots or automated systems previously discussed or by another suitable robot or machine. The forces may be predetermined or may be measured or monitored as they are applied. The forces may be applied using one or more than one member or device for exerting one or more than one force on each sample. Alternatively, one member or device may exert one or more forces on a plurality of samples.

Responses of the materials may include the tack or adhesive forces exhibited by the materials in response to forces provided by the members. The responses may also include the deformation of the materials in response to the forces provided by the members. Suitable sensors may be used to measure the deformation of the materials such as visual, optical, resistive, thermal or other sensors. One or more sensors may be used to monitor each sample. Alternatively, sensors may be used to monitor a plurality of samples.

Adhesiveness may be determined for example, by relating the deformation and/or the forces applied by the members to the adhesiveness of the materials. Adhesiveness properties may be determined using a variety of engineering equations to relate responses of the materials to the adhesive properties of the materials. As an example, a law such as Stephen's law of Tack may be used:

$$\text{Tack} = (\text{Area})(\text{Viscosity})(\text{Speed})/(\text{Distance})^3$$

wherein area refers to the contact area between a member and a material, viscosity is the viscosity of the material, speed is the rate at which the member is moved away from the material and distance is the distance from the contact surface of the member used for contacting the materials to the contact surface of another member (e.g. a substrate) to which the materials are contacted or attached.

Figure 5:
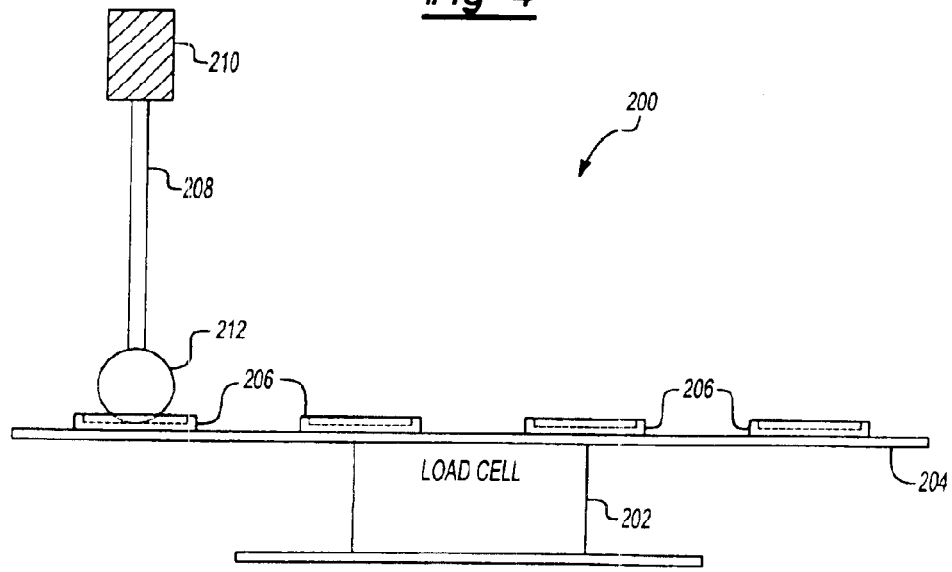
FIG. 5 is a schematic of a system for assisting in determining mechanical properties of materials in accordance with the present invention.

Referring to FIG. 5, there is illustrated a system 200 including a load cell 202 supporting a substrate 204, which, in turn is supporting a plurality of samples 206. An appropriate probe 208 is located adjacent the substrate 204 for applying forces to the samples 206. Preferably, the probe 208 includes a surface for contacting the samples 206 provided by a contacting portion 212 to allow the samples 206 to adhesively secure themselves to the probe 208. In one highly preferred embodiment, the contacting portion 212 may be a loop of flexible material wherein the pressure or force with which the loop contacts the samples 206 is dependent upon the flexure or stiffness of the loop, thus making the contacting force controllable. Thereafter, the probe 208 is moved away from the samples 206 to displace or strain the samples and/or to oppose adhesive forces of the samples 206. Preferably, the probe 208 includes a distance measuring device 210, such as a soft spring, for determining the distance that a contacting portion 212 of the probe 208 displaces at least a portion of the samples 206 for a given amount of force applied by the probe 208. In a preferred embodiment, the probe 208 could be moved by a robot or other automated system (not shown) to provide a force upon each of the samples 206 and the load cell 202 and the distance measuring device 210 could be in communication with the data acquisition hardware/software to collect data there from so that a tack or other adhesive measurement could be determined for each sample 206.

Figure 5A:
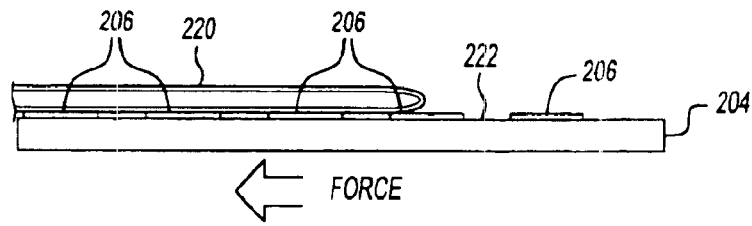
FIGS. 5(a)–5(c) are schematics of alternative systems for assisting in determining mechanical properties in accordance with the present invention.
Figure 5B:
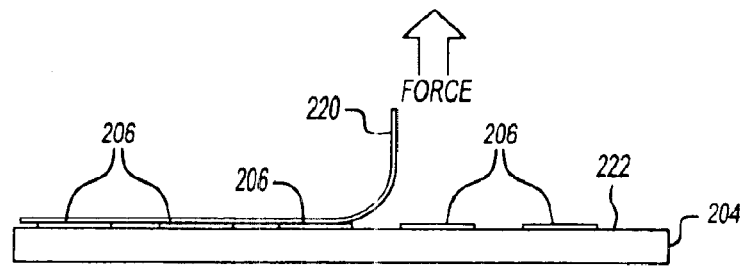
Figure 5C:
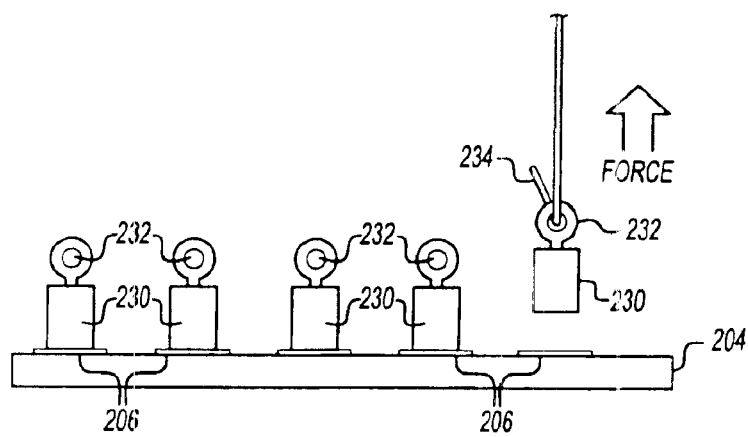

Referring to FIGS. 5(a)–5(c), there are illustrated alternative probes for providing alternative forces to the samples 206. In FIG. 5(a), a flexible probe 220 is used for peel testing a plurality of samples 206. The flexible probe 220 (e.g., a flexible sheet or tape) is adhesively secured to a plurality of samples 206 wherein the samples 206 are secured to a surface 222 of the substrate 204. According to one embodiment, a plurality of flexible probes 220 may be laid upon a plurality of rows of samples 206. Alternatively, a flexible sheet may be laid upon a plurality of samples and the sheet may be cut (e.g., with one or more razors mounted to a handle, a scalpel or the like) so that the probes 220 are adhered to individual rows of samples. Once in place, one or more probes 220 are pulled off of each sample 206 by a force applied to the probe 220. The probes 220 may be pulled off in any desired direction or at any desired angle. Alternatively the substrate 204 may be moved relative to the probes 220. In FIG. 5(a), the probe 220 is pulled of in a direction that is substantially parallel to a surface 222 of the substrate 204, to which the samples 206 are secured. In FIG. 5(b), the probe 220 is pulled off of the sample 206 by a force applied to the probe 220 in a direction substantially perpendicular to the surface 222 of the substrate 204. Preferably, the probes 220 are pulled off the samples 206 automatically by an automatic system (not shown) such as a robot arm and are pulled off in a predetermined direction, at a predetermined angle or both. Either, the probe 220, the automatic system or both may be fitted with one or more mechanisms to allow the automatic system to releasably secure itself to the probes 220. Exemplary releasable attachments may comprise a hook attached to the automated system and a loop formed in the probe 220 or other such mechanisms. It is also preferable for either the automatic system or the substrate 206 to include a force measuring device or sensor (not shown) such as a load cell or other sensor for determining the amount of force needed to remove the probes 220 from the samples 206.

In FIG. 5(c), several probes 230 are individually adhesively secured each to a different sample 206. The weight of the probes 230 by be predetermined to provide a desired contacting pressure and the probes 230 may be allowed to set upon the samples 206 for a predetermined amount of desired contacting time. In this manner, the degree of adhesiveness or tack of the samples may be determined for such contacting times and pressures which may be critical or not critical depending upon the desired application of the sample materials. Preferably, each of the members 230 includes a mechanism for removing the member 230 from the samples 206. For instance, each member 230 may include a loop 232 attached to it such that a hook 234, preferably attached to a robot or other automated system that can pull each member off of its respective sample 206 thereby providing a force to the sample 206. Again, either the automated system or the substrate 204 is preferably fitted with a force sensor to determine the force used to move or remove the probes 230 from the samples 206.

In certain circumstances, it may be desirable to obtain measurements of the adhesiveness of material samples in terms of shear strength (i.e., the resistance of an adhesive bond against forces acting along or parallel to the plane of the bond). In such circumstances, one or more members or probes such as chips, fabrics, dies or non-adhesive tapes may be placed such that a surface of the members contacts each of a set of material samples. Preferably, each of the members include a releasable attachment that can be engaged by an automatic system (e.g., a robot arm). Thereafter, the automatic system, which is preferably fitted with a force sensor can apply a force parallel to the plane of the surface of the members contacting the sample. As the force is applied, it can be measured and monitored using the sensor preferably as a graphed profile of force versus time. The force applied to the members may or may not remove the members from the material samples.

In any or all of the above embodiments adhesive properties may be quantified in terms of forces applied. Forces applied per unit surface area of sample or otherwise quantified.

In between measurements of samples, especially when the samples have a tendency to leave residue upon a probe, the probe may be cleaned or a portion (e.g., a contacting portion) of the probe may be replaced to assure accurate readings. Probes may be cleaned between testing of samples. For examples, the probes may be immersed in a cleaning solution, the probes may be exposed to a cleaning surface (e.g., a buffing wheel, cleaning pad or the like) or other techniques may be used. Alternatively, portions of probes or entire probes may be replaced between testing of samples. For instance, disposable probe tips such as balls, members or the like may be releasably attached to a probe (e.g., by suction, magnet or otherwise) such that the tips may be quickly attached and released from a probe, robot arm or both between testing of samples. As another example, and particularly for the peel testing, flexible non-adhesive tape-like probes may be provided and replaced with a system of rollers, pulleys, cams or the like. To assure the cleanliness of the probe, a tack or adhesive measurement may be performed on a clean non-tacky, non-adhesive surface and, preferably, there is no adhesiveness measured for the clean surface thereby assuring that the probe has been properly cleaned, however, the presence of adhesiveness can indicate that the probe needs to be cleaned further or cleaned another way.

It will be appreciated that any number of additional stimuli may be introduced and the effects of which analyzed. For example, various environmental conditions such as humidity, temperature, pressure and the like may be altered (e.g., raised or lowered) surrounding the sample materials to vary tests of the sample materials.

Sample-Throughput

For methods directed to characterizing a plurality of samples, a property of each of the samples or of one or more components thereof is detected—serially or in a parallel, serial-parallel or hybrid parallel-serial manner—at an average sample throughput of not more than about 10 minutes per sample. As used in connection herewith, the term "average sample throughput" refers to the sample-number normalized total (cumulative) period of time required to detect a property of two or more samples with a characterization system. The total, cumulative time period is delineated from the initiation of the characterization process for the first sample, to the detection of a property of the last sample or of a component thereof, and includes any intervening between-sample pauses in the process. The sample throughput is more preferably not more than about 8 minutes per sample, even more preferably not more than about 4 minutes per sample and still more preferably not more than about 2 minutes per sample. Depending on the quality resolution of the characterizing information required, the average sample throughput can be not more than about 1 minute per sample, and if desired, not more than about 30 seconds per sample, not more than about 20 seconds per sample or not more than about 10 seconds per sample, and in some applications, not more than about 5 seconds per sample and not more than about 1 second per sample. Sample-throughput values of less than 4 minutes, less than 2 minutes, less than 1 minute, less than 30 seconds, less than 20 seconds and less than 10 seconds are demonstrated in the examples. The average sample-throughput preferably ranges from about 10 minutes per sample to about 10 seconds per sample, more preferably from about 8 minutes per sample to about 10 seconds per sample, even more preferably from about 4 minutes per sample to about 10 seconds per sample and, in some applications, most preferably from about 2 minutes per sample to about 10 seconds per sample.

A sample-throughput of 10 minutes per sample or less is important for a number of reasons. Systems that detect a property of a sample or of a component thereof at the aforementioned sample throughput rates can be employed effectively in a combinatorial research program. From a completely practical point of view, the characterization rates are also roughly commensurate with reasonably-scaled polymer sample library synthesis rates. It is generally desirable that combinatorial screening systems, such as the polymer characterization protocols disclosed herein, operate with roughly the same sample throughput as combinatorial synthesis protocols—to prevent a backlog of uncharacterized polymerization product samples. Hence, because moderate scale polymer-synthesis systems, such as the Discovery Tools™ PPR-48™ (Symyx Technologies, Santa Clara Calif.), can readily prepare polymer libraries with a sample-throughput of about 100 polymer samples per day, a screening throughput of about 10 minutes per sample or faster is desirable. Higher throughput synthesis systems demand higher characterization throughputs. The preferred higher throughput values are also important with respect to process control applications, to provide near-real time control data.

Additionally, as shown in connection with the examples provided herein, the characterization of polymer samples at such throughputs can offer sufficiently rigorous quality of data, to be useful for scientifically meaningful exploration of the material compositional and/or reaction conditions research space.

Hence, the average sample-throughput can range, in preferred cases, from about 10 minutes per sample to about 8 minutes per sample, from about 8 minutes per sample to about 2 minutes per sample, from about 2 minutes per sample to about 1 minute per sample, from about 1 minute per sample to about 30 seconds per sample and from about 1 minute per sample to about 10 seconds per sample, with preferences depending on the quality of resolution required in a particular case. For example, in some research strategies, the very high sample throughputs can be effectively employed to efficiently screen a polymer sample or component thereof having a particularly desired property (e.g., such as weight-average molecular weight). In short, the search can be accelerated for the particular property of research interest.

Calibration Methods and Standards

As desired the systems and methods of the present invention may optionally employ a calibration procedure. By way of example, a calibration standard is provided having a number of subcomponents that differ with respect to strength of a material. Such subcomponents are typically referred to as "known standards" or, simply, "standards" that are well characterized with respect to the calibrating property of interest. They are analyzed by the measuring apparatus of the present invention and the apparatus is adjusted as desired.

The accuracy and precision of the determination of material properties can vary depending on the type of measurement being conducted, the purpose of the measurements and the like. According to one embodiment the response, the stimulus or both applied to each of the material samples of the samples may be ranked or indexed and the ranked or indexed properties may be compared with each other. In such a case, accuracy and precision with regard to determining exact values of the properties of the sample materials may not be as important as assuring that the tests are performed consistently upon samples that are compared to each other since the object of the testing may be to determine which materials perform best rather than determining exact material properties. In other cases, such as when the stimuli and responses of the sample materials will be used to compare the sample materials to known properties of known materials, it may be more important to determine values for sample material properties such as Young's Modulus, shear modulus, tensile strength tack and the like that are closer to the absolute values of those properties for the sample materials to allow useful comparison's. The skilled artisan will recognize that the methods and apparatuses discussed above can be configured to be more or less accurate depending upon the equipment used and that the choice of equipment can depend on constraints such as monetary constraint and upon the amount of accuracy needed for a particular purpose.

Accuracy and precision for measurement of sample materials especially the deformation or displacement of the materials may also depend upon the nature of the samples being tested. Inherently, the instrumentation and testing equipment such as probes, robotic arms and substrates experience various amounts of deformation or strain as they apply a force to a sample material and, depending of the accuracy need or desired, that deformation or strain may need to be accounted for. Typically, softer materials such as gels, elastomers and the like tend to deform to a substantially greater degree than the instrumentation and testing equipment such that the deformation or strain of the latter may be inconsequential. However, more rigid sample materials such as plastics and the like can deform much less than the instrumentation and testing equipment. Therefore, for testing relatively rigid sample materials, it may be desirable to use rigid equipment for providing force to a sample or it may be desirable to measure the deformation of the sample with equipment that is separate from the equipment providing the force to the samples. Alternatively, it may be desirable to use a transducer mounted to a probe or other instrumentation for measuring total deformation of the testing equipment and the samples coupled with determination of the deformation of the testing equipment such that the deformation of the testing equipment may be subtracted from the total deformation to determine the deformation of the sample materials.

As an example, methods of the present invention may be performed using a probe mounted to an arm of an XYZ liquid handling robot. The arm carrying the probe, if supported only at one end, may flex or bend about the pivot point where the arm is supported. If the arm is supported at both ends, it may still bow in the middle when a force is applied to it. Thus is may be desirable to monitor the displacement of the probe relative to the arm using an additional sensor to precisely measure the displacement of the probe relative to the sample. Alternatively the deformation of the probe relative to the arm may be calculated for a variety of forces to determine a relationship between force and deformation of the probe. Such relationship may be plotted as a force-distance curve of the arm, supporting member, etc. Then, when a force is generated upon the sample, the corresponding deformation of the probe can be calculated and subtracted from the total deformation of the probe and the sample, to give the sample deformation.

As another example, a transducer or sensor may be used that is substantially unaffected by the strain or deformation of the equipment (e.g., the probe or robotic arm) being used to make measurements of sample materials. One example of such a sensor is a Linear Variable Displacement Transducer (LVDT), which may be assembled to the end of a probe or other equipment. Typically the LVDT will include a first portion that can be located in a stationary position relative to a substrate upon which one or more sample material are attached. Additionally, the LVDT may include a second portion that can be located in a stationary position relative to a surface (e.g., of a probe) that contacts the material samples for causing displacement of the samples. Thereafter, the LVDT only senses the movement of its first portion relative to its second portion wherein such movement is a direct measurement of the deformation or strain of a material sample since each of the first and second portions of the LVDT can only move relative to each other as much as the material sample deforms to allow movement between the surface to which the second portion is attached and the substrate to which the first portion is attached. In one example, the LVDT is a coil assembly with a push rod that can be rigidly attached to a probe directly adjacent to a surface of the probe that is configured for contacting samples. Thereafter, for testing material samples, the push rod contacts a substrate supporting material samples as the probe contacts the samples. As the probe is pushed against the sample, the LVDT rod is stationary relative to the substrate, but is moved into the coil assembly a distance that directly corresponds to the displacement of the surface of the probe, which in turn, corresponds to the deformation of each sample regardless of the deformation of the probe, robot or both.

Other Screens

The present invention may be employed by itself or in combination with other screening protocols for the analysis of liquids or their constituents. Without limitation, examples of such screening techniques include those addressed in commonly-owned U.S. Pat. Nos. 6,182,499 (McFarland et al); 6,175,409 B1 (Nielsen et al); 6,157,449 (Hajduk et al); 6,151,123 (Nielsen); 6,034,775 (McFarland et al); 5,959,297 (Weinberg et al), 5,776,359 (Schultz et al.), all of which are hereby expressly incorporated by reference herein.

Screening techniques may also include (without limitation) optical screening, infrared screening, electrochemical screening, flow characterization (e.g., gas, liquid or gel-phase chromatography), spectrometry, crystallography, or the like.

Sample materials of gels that are formed from Knox Gelatine. Knox Gelatine brand gelatin is dissolved in hot water at various concentrations, and equal volumes (300 ul each) are placed in the wells of a microtiter plate and refrigerated overnight. The samples are then sequentially probed with a 3/16" diameter stainless steel probe with a rounded end. The probe is placed above the gel surface of each of the sample materials and moved downward at a velocity of 5 mm/second while the force is recorded. The recorded force for each sample initially increases at a regular rate. Then the regular rate experiences a sudden decrease indicating failure of each of the material samples (i.e., gel strength failure). The measurement thus provides information on both elastic and failure properties of each of the sample materials. The force applied to each of the samples can be graphed or otherwise visually displayed versus time for data analysis purposes.

It should be understood that the invention is not limited to the exact embodiment or construction which has been illustrated and described but that various changes may be made without departing from the spirit and the scope of the invention.

What is claimed is:

1. A method for screening an array of materials for one or more adhesive properties, comprising:
   providing a library of at least four sample materials;
   contacting the at least four sample materials with at least one member for applying one or more forces to the at least four sample materials in opposition to the one or more adhesive properties of the at least four sample materials wherein the at least one member is moved by an automatic system for applying the one or more forces;
   monitoring a response of each of the at least four sample materials to the one or more forces; and
   correlating the response of the each of the at least four sample materials to the one or more adhesive properties of the each of the at least four sample materials.

2. A method as in claim 1, wherein the step of providing a library of at least four sample materials includes attaching each of the at least four sample materials to a single substrate.

3. A method as in claim 2, further comprising raising the temperature of the at least four sample materials prior to applying the one or more forces to the at least four sample materials.

4. A method as in claim 2, further comprising lowering the temperature of the at least four sample materials prior to applying the one or more forces to the at least four sample materials.

5. A method as in claim 2, wherein a first of said one or more forces is applied to a first of the at least four sample materials no more than five minutes previous to applying a second of said one or more forces to a second of the at least four sample materials.

6. A method as in claim 1, wherein said library includes at least 16 different sample materials.

7. A method as in claim 1, wherein at least one of the at least four sample materials is a polymer.

8. A method as in claim 1, wherein the at least four sample materials are gels.

9. A method as in claim 1, wherein the one or more forces places a tensile stress upon the at least four sample materials.

10. A method as in claim 1, wherein the one or more forces are applied with a probe having a flexible contacting portion.

11. A method as in claim 1, wherein said library includes at least 16 different materials, each attached to a single substrate and wherein the throughput rate of testing the at least 16 different materials is no greater than 10 minutes per material.

12. A method as in claim 1, wherein the automatic system includes a robot arm.

13. A method for measuring an adhesive property of a plurality of sample materials, the method comprising the steps of:

providing a library comprising at least four different sample materials; and serially measuring the adhesive property of each of the at least four different sample materials at a throughput rate no greater than about 5 minutes per sample material.

14. A method as in claim 13, wherein the library includes at least 8 different sample materials.

15. A method as in claim 13, wherein the library includes at least 16 different sample materials.

16. The method of claim 13, wherein the adhesive property of the at least four sample materials is measured at an average sample-throughput of not more than about 2 minutes per sample material.

17. The method of claim 13 wherein the library comprises at least 8 sample materials and at least about 50% of the at least 8 sample materials are different from each other.

18. The method of claim 13, wherein the library comprises at least 16 sample materials and at least 75% of the at least 16 sample materials are different from each other.

19. The method of claim 13, wherein the at least four sample materials are members of a combinatorial library of polymerization product mixtures.

20. A method for screening an array of materials for one or more adhesive properties, comprising:

providing a library of at least 16 sample materials wherein each of the at least 16 sample materials is physically attached to a single substrate;

contacting the at least 16 sample materials with at least one member such that the at least 16 sample materials adhesively secure themselves to the at least one member wherein the at least one member includes a flexible portion for assisting in controlling the amount of force with which the at least one member contacts the at least 16 sample materials and wherein a first sample material is contacted by the at least one member no more than 8 minutes prior to contacting a second sample material of the at least 16 sample materials;

moving the at least one member away from the at least 16 sample materials with a robot arm for applying one or more forces to the at least 16 sample materials in opposition to the one or more adhesive properties of the at least 16 sample materials wherein the at least one member is moved;

monitoring the amounts of force required to separate the at least one member from the at least 16 sample materials using one or more load cells;

correlating the amounts of force required to separate the at least one member from the at least 16 sample materials to the one or more adhesive properties of the each of the at least four sample materials; and ranking the adhesive properties of the each of the at least 16 sample materials relative to each other.

* * * * *

UNITED STATES PATENT AND TRADEMARK OFFICE
CERTIFICATE OF CORRECTION

PATENT NO. : 6,951,144 B2
DATED : October 4, 2005
INVENTOR(S) : Paul Mansky

It is certified that error appears in the above-identified patent and that said Letters Patent is hereby corrected as shown below:

Title page,
Item [56], References Cited, FOREIGN PATENT DOCUMENTS, insert:
-- EP   0317356 A2       5/1989
　JP   40 2297040 A     12/1990
　WO   96/11878 A1       4/1996
　WO   98/15501 A2       4/1998
　WO   99/18431 A1       4/1999
　WO   00/17413 A2       3/2000
　WO   00/23921 A1       4/2000
　WO   00/36410 A1       6/2000
　WO   00/40331 A1       7/2000
　WO   00/51720 A2       9/2000
　WO   00/67086 A1      11/2000
　WO   01/79949 A2      10/2001 --.

OTHER PUBLICATIONS, insert:
-- U.S. Appl. No. 09/305,830 entitled "Synthesizing Combinatorial Libraries of Materials" (Rust et al.) filed on May 5, 1999

The family of applications for U.S. Appl. No. 09/227,558 entitled "Apparatus and Method of Research for Creating and Testing Novel Catalysts, Reactions and Polymers" (Turner et al.) filed January 8, 1999

The family of applications for U.S. Appl. No. 09/211,982 entitled "Parallel Reactor With Internal Sensing" (Turner et al.) filed December 14, 1998

U.S. Appl. No. 09/235,368 entitled "Polymerization Method From The Combinatorial Synthesis and Analysis of Organometallic Compounds and Catalysts" (Weinberg et al.) filed January 21, 1999

U.S. Prov. Appl. No. 60/122,704 entitled "Controlled, Stable Free Radical Emulsion and Water-Based Polymerizations" (Klaerner et al.) filed March 9, 1999

U.S. Appl. No. 09/579,338 entitled "Rheo-Optical Indexer and Method of Screening and Characterizing Arrays of Materials" (Carlson et al.) filed May 25, 2000

U.S. Appl. No. 09/578,997 entitled "High Throughput Viscometer and Method of Using Same" filed May 25, 2000

UNITED STATES PATENT AND TRADEMARK OFFICE
CERTIFICATE OF CORRECTION

PATENT NO. : 6,951,144 B2
DATED : October 4, 2005
INVENTOR(S) : Paul Mansky

It is certified that error appears in the above-identified patent and that said Letters Patent is hereby corrected as shown below:

Title page (cont'd),
PCT Appl. No. PCT/US01/11417 entitled "Automated Process Control and Data Management System and Methods", filed April 6, 2001 --; and
"Pan, Ning and K.C. Yen," reference should read:
-- Pan, Ning and K.C. Yen, "Physical Interpretations of Curves Obtained Through the Fabric Extraction Process for Handle Measurement," Textile Research Journal 62(5), pp. 279-290 (1992). --.

Signed and Sealed this

Seventh Day of March, 2006

JON W. DUDAS
*Director of the United States Patent and Trademark Office*